(12) United States Patent
Prevost et al.

(10) Patent No.: US 7,196,084 B2
(45) Date of Patent: Mar. 27, 2007

(54) CDC25 PHOSPHATASE INHIBITORS

(75) Inventors: Grégoire Prevost, Antony (FR); Marie-Christine Brezak Pannetier, Antony (FR); Marie-Odile Galcera Contour, Bondoufle (FR); Christophe Thurieau, Paris (FR); Françoise Goubin Gramatica, Agen (FR); Bernard Ducommun, Belberaud (FR); Christophe Lanco, Dourdan (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 497 days.

(21) Appl. No.: 10/343,171

(22) PCT Filed: Jul. 26, 2001

(86) PCT No.: PCT/FR01/02443

§ 371 (c)(1),
(2), (4) Date: Jan. 27, 2003

(87) PCT Pub. No.: WO02/09686

PCT Pub. Date: Feb. 7, 2002

(65) Prior Publication Data

US 2004/0034103 A1    Feb. 19, 2004

(30) Foreign Application Priority Data

Jul. 28, 2000   (FR)   ................. 00 09900

(51) Int. Cl.
- A01N 43/58 (2006.01)
- A61K 31/50 (2006.01)
- C07D 237/02 (2006.01)
- C07D 295/00 (2006.01)

(52) U.S. Cl. ............ 514/247; 544/224; 544/336; 540/450; 540/484; 514/218

(58) Field of Classification Search ............ 544/224, 544/336; 540/450, 484; 514/218, 247
See application file for complete search history.

(56) References Cited

U.S. PATENT DOCUMENTS 4,032,635 A    6/1977    Umezawa et al.

FOREIGN PATENT DOCUMENTS

| WO | 9505363 | 2/1995 |
| WO | 9842696 | 10/1998 |
| WO | 0017190 | 3/2000 |

OTHER PUBLICATIONS

Lis et al. "Synthesis of Novel Aryloxy- Propanolamines . . . ", Journal of Medicinal Chemistry, (1990), 33 (10), 2883-91.*

Bourhim et al, "Design . . . Retrobenzamides", Arzneim.-Forsch. (1999), 49(2), 81-87, XP000992843.

Yamagami et al, "A Quantitative . . . Phenylacetanilides", Hem. Pharm. Bull., vol. 32, No. 12, 1984, pp. 5003-5009, XP002166155.

Database Chemabs en ligne! Chemical Abstracts Service, Columbus, Ohio, US: Fujisawa Pharmaceutical Co., Ltd., Japan: Preparation of biphenyl compounds as drugs: retrieved from STN Database accession No. 115; 114130 XP002166157.

"The Merck Index"1996, Merck & Co., Inc. XP002166156, Niclosamide p. 1118.

Database Chemabs 'en'ligne! Chemical Abstracts Service, Columbus, Ohio, US: Umezawa Hamao et al: "Benzanilide Derviatives" retrieved from STN Database accession No. 87:5662 XP002166158.

Coburn et al, "Potential . . . Viscosus" J. Med. Chem., vol. 24, 1981 pp. 1245-1249, Jan. 28, 2003.

* cited by examiner

Primary Examiner—James O. Wilson
Assistant Examiner—Paul V. Ward
(74) Attorney, Agent, or Firm—Charles A. Muserlian

(57) ABSTRACT

The invention concerns novel cdc25 phosphatase inhibitors, and in particular cdc25-C, which correspond to the general formula (I) wherein: A represents a carbocyclic aryl radical optionally substituted 1 to 3 times by one or more radicals independently selected among a halogen atom and an alkyl, hydroxy, alkoxy, alkylthio or $NR^1R^2$ radical wherein $R^1$ and $R^2$ represent a hydrogen atom or an alkyl radical or $R^1$ and $R^2$ form together with the nitrogen atom a heterocycle of 4 to 7 members comprising 1 to 2 heteroatoms, the members required to complete the heterocycle being selected independently among the $CR^3R^4$—, —O—, —S and $NR^5$-radicals, $R^3$ and $R^4$ representing independently each time they are involved a hydrogen atom or an alkyl, hydroxy, alkoxy, amino, alkylamino or dialkylamino radical, and $R_5$ representing independently each time it is involved a hydrogen atom or an alkyl radical, or A represents a phenyl radical substituted by a phenyl radical optionally substituted 1 to 3 times by one or more radicals selected independently among a halogen atom and an alkyl, hydroxy, alkoxy, alkylthio or $NR^1R^2$ radical wherein $R^1$ and $R^2$ represent a hydrogen atom or an alkyl radical; B represents a —$(CH_2)_i$—(CO)— or —NH—CO—$(CH_2)_n$ or —$(CH_2)_p$ and i and n being integers from 0 to 2 and p being an integer from 0 to 1; W represents a hydrogen atom or an alkyl radical; X represents a —$(CH_2)_q$— or $(CH_2)_j$—CO—$(CH_2)_r$—, q being an integer from 1 to 4 and j and r being integers from 0 to 6; Y represents in particular a nitrophenyl, aminophenyl, alkylaminophenyl or dialkylaminophenyl radical or the radical (T)

(I)

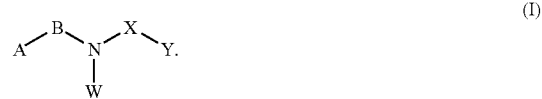

9 Claims, 1 Drawing Sheet

CDC25 PHOSPHATASE INHIBITORS

Figure 1:
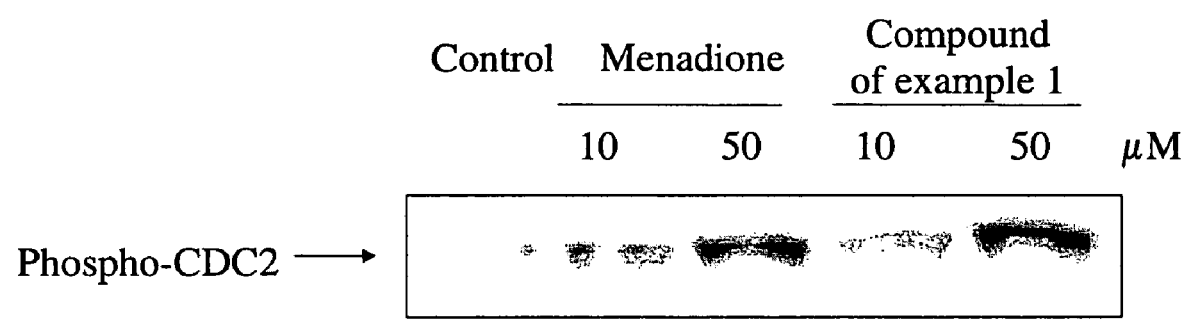

This application is a 371 of PCT/FR01/02443 filed Jul. 26, 2001.

A subject of the present invention is new inhibitors of cdc25 phosphatases, and in particular of cdc25-C phosphatase.

Control of the transition between the different phases of the cell cycle during mitosis or meiosis is provided by a group of proteins, the enzymatic activities of which are associated with different states of phosphorylation. These states are controlled by two large classes of enzymes: the kinases and the phosphatases.

Synchronization of the different phases of the cell cycle thus allows reorganisation of the cell architecture at each cycle in all of the living world (microorganisms, yeasts, vertebrates, plants). Among the kinases, the cyclin-dependent kinases (CDKs) play a major role in this control of the cell cycle. Their activities are regulated by their molecular associations with other proteins called cyclins. In addition, endogenous inhibitors are capable of preventing these activities. Several inhibitors of this family of kinases are already identified and studied in several therapeutic fields such as oncology for preventing the division of tumour cells (McDonald and el-Deiry, Int. J. Oncol. (2000), 16, 871–886) or also neurobiology for preventing natural or chemically-induced apoptosis of normal cells (for example the neurones) (cf. Maas et al., J. Neurochem. (1998), 70, 1401–1410; Park et al., J. Neurosci. (1997) 17, 1256–1270).

Moreover, the enzymatic activity of these different CDKs is controlled by two other families of enzymes which work in opposition (Jessus and Ozon, Prog. Cell cycle Res. (1995), 1, 215–228). The first groups together kinases such as Wee1 and Mik1 which deactivate the CDKs by phosphorylating certain amino acids (Den Haese et al., Mol. Biol. Cell (1995), 6, 371–385). The second groups together phosphatases such as Cdc25 which activate the CDKs by dephosphorylating tyrosine and threonine residues of CDKs (Gould et al., Science (1990), 250, 1573–1576). Dephosphorylation will be carried out in the first instance thanks to a protein/protein interaction between the cyclin and cdc25, and this complex will in the second instance target CDK (Morris and Divita, J. Mol. Biol. (1999), 286, 475–487). In addition, cyclin B is itself phosphorylated by the Cdc2 kinase (cdk1) to which it is associated (Borgne et al., J. Biol. Chem. (1999), 274, 11977–11986).

If a single form of cdc25 is described in yeast, a family of 3 genes, cdc25-A, cdc25-B and cdc25-C, code for the human cdc25 proteins. In addition, variants originating from alternative splicing of the cdc25B gene have been identified: they are cdc25B1, cdc25B2 and cdc25B3 (Baldin et al., Oncogene (1997), 14, 2485–2495). The proteins coded by these variants would be localized differently within the cell (Davezac et al., Oncogene (2000), 19, 2179–2185). cdc25 activity is regulated by the Cdc2 and Cdk2 kinases. But in the absence of cdc2 kinase, the activity of cdc25 can be activated by other kinases (Izumi and Maller, Mol. Biol. Cell (1995), 6, 215–226). Among these, the chk1 protein phosphorylates cdc25-C on a serine in position 216, which increases its affinity for a chaperone protein 14-3-3. This bond neutralises cdc25-C and consequently maintains the cdk1 enzyme in a phosphorylated state and therefore inactive, not allowing entry into mitosis. The chaperone protein allows the complex to pass into the cytoplasm thanks to a protein unit of nuclear export (Lopez-Girona et al., Nature (1999), 397, 172–175).

A chemical inhibitor of chk1 (SB-218070) allows a cell to continue its cell cycle despite the induction of the DNA break. This aspect allows the effectiveness of certain cytotoxic compounds such as campthotecin to be increased (Jackson et al., Cancer Res. (2000), 60, 566–572).

The role of cdc25 phosphatases in oncogenesis was described initially by the Beach group showing that cdc25A and cdc25B by co-operating with Ha-RASG12V form foci after transfection of normal cells (Galaktionov et al., Science (1995), 269, 1575–1577). The transforming activity of cdc25A and cdc25B is also observed when transfection is carried out in cells having a lack of the RB1 tumour suppressor gene. In addition, the expression of the cdc25-A and -B genes appears to be under the direct control of the protein coded by the c-Myc oncogene (Galaktionov et al., Nature (1996), 382, 511-517). On the other hand, cdc25-C phosphatase does not seem to be controlled by the latter.

The overexpression of cdc25, and principally cdc25-A, appears to prevent the cell from stopping its cell cycle in the event of aggression on the genome and thus avoids a possible repair process (Mailand et al., Science (2000), 288, 1425–1429).

Moreover, the overexpression of the different forms of cdc25 is now reported in many classifications of human tumors:

Breast cancer: measurement by riboprobe shows that 32% of tumors over-express cdc25-B. The overexpression of cdc25-A is shown in nearly 50% of cancers of the breast and is associated with a poor prognosis (Cangi et al., Résumé 2984, AACR meeting San Francisco, 2000).

Lymphomas: in the circulating lymphocytes, the expressions of the RNAs of cdc25-B1 and -B3 are detected by RT-PCR while the expressions of cdc25-A, -B2 and -C are very weak or undetectable. On the other hand, analysis of these genes in non-hodgkin's lymphomas shows a strong expression of cdc25-A and -B2 in approximately 35% of the tumors. The cdc25-B1 and -B3 variants are themselves detected in all of the tumors analysed. On the other hand, the expression of cdc25-C remains very weak in the sample group (Hernandez et al., Int. J. Cancer (2000), 89, 148–152). It is important to note the correlation between the expression of proteins such as myc and cdc25. 26 of 35 (74%) non-hodgkin's lymphomas with a raised level of cdc25-B also show an overexpression of c-myc. On the other hand, 27 out of 28 (96%) tumors with a low level of cdc25-B expression do not show any detectable c-myc (P<0.0001). This suggests that the expression of cdc25 associated with that of myc could participate in the development of this type of lymphoma (Hernandez et al., Cancer Res. (1998), 58, 17621767).

Neck and head cancers: of 20 tumors examined by quantitative RT-PCR, Gasparotto et al. note that CDC25-A and -B are over-expressed whilst cdc25-C is expressed very little (Gasparotto et al., Cancer Res. (1997), 57, 2366–2368).

Moreover, the E. Sausville group reports an inverse correlation between the level of expression of cdc25-B in a panel of 60 cell lines and their sensitivity to CDK inhibitors such as Olumucine or Flavopiridol, suggesting that the presence of cdc25 can provide resistance to certain anti-tumor agents and more particularly to CDK inhibitors (Hose et al., Proceedings of AACR, Abstract 3571, San Francisco, 2000).

Vitamin K3, also called menadione, was the first selective inhibitor of cdc25 phosphatase described (Ham et al.,

*Bioorg. Med. Chem. Lett.* (1998) 8, 2507–2510). Other cdc25 inhibitors have since been identified and have an inhibitory activity of micromolar order on the recombinant enzymes. Among these products, the following can be noted:

1. Naphthoquinone analogues derived from menadione (Ham et al., *Bioorg. Med. Chem. Lett.* (1998) 8, 2507–2510).
2. Cpd5, a thioalkyl derivative of vitamin K (Tamura et al., *Cancer Res.* (2000), 60, 1317–1325). The inhibition constants (Kis) measured on cdc25-A, -B2 & -C are 15, 1.7 and 1.3 μmol respectively.
3. 4-(benzyl-(2-[(2,5-diphenyl-oxazole-4-carbonyl)-amino]-ethyl)-carbamoyl)-2-decanoylaminobutanoic acid also called SC-alpha alpha delta 9 (Tamura et al., *Oncogene* (1999) 18, 6989–6996).
4. Certain compounds originating from a Ugi library containing groups mimicking phosphates are non-competitive inhibitors of cdc25-A which do not act on the active site. The most active compound has an $IC_{50}$ of 0.5 μM and the interaction site is in the process of being identified (Bergnes et al., *Bioorg. Med. Chem. Lett.* (1999), 9, 2849–2854).
5. Quinolin-4-one and 1,7-naphthyridin-4-one derivatives. Certain compounds are inhibitors both of cdc25 and cdc2 (el-Subbagh et al., *Arch. Pharm.* (*Weinheim.*) (1999), 332, 19–24).
6. Dysidiolide and derivatives containing a γ-hydroxy butenolide group. The effectiveness of these products is discussed in Blanchard et al., *Bioorg. Med. Chem. Lett.* (1999), 9, 2537–2538.
7. Certain 5-substituted 2-bromoindolo[3,2-b]quinoxalines. Certain of these compounds are inhibitors of both cdc25 and cdc2 (Abadi et al., *Arch. Pharm.* (*Weinheim.*) (1998), 331, 352–358).

The PCT Application WO 00/17190 describes amidine derivatives which inhibit the NO synthases and trap the free radicals. Because of this, these compounds present numerous pharmacological properties and their use can be envisaged in the treatment of numerous pathologies, principally in the field of neurology. A simplified general formula of these compounds could be general formula (ET1):

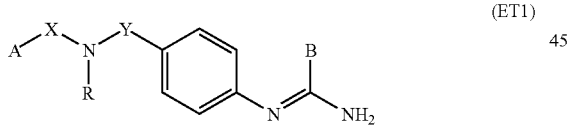
(ET1)

in which
A represents a radical which traps free radicals, for example a substituted phenyl radical;
X and Y are linking chains, for example alkylene, alkylenecarbonyl, carbonylalkylene radicals;
R represents H or alkyl; and
B represents a carbocyclic or heterocyclic aryl radical, and preferably the 2-thienyl radical.

The invention offers new inhibitors of cdc25, and in particular of cdc25-C, which correspond to general formula (I) defined below. These compounds are capable of being used as medicaments, in particular in the treatment of the following diseases/disorders:
inhibition of tumorous proliferation when used alone or in combination with other treatments;
inhibition of the proliferation of normal cells when used alone or in combination with other treatments;
the prevention of spontaneous alopecia;
the prevention of alopecia induced by exogenous products;
the prevention of radiation-induced alopecia;
the prevention of spontaneous or induced apoptosis of normal cells; the prevention of meiosis and fertilization;
the prevention of oocyte maturation;
all of the diseases/disorders corresponding to the uses mentioned for CDK inhibitors, and in particular non-tumorous proliferative diseases (for example: angiogenesis, psoriasis or the recurrence of stenosis), tumorous proliferative diseases, parasitology (proliferation of protozoa), viral infections, neurodegenerative diseases, myopathies;
all of the diseases/disorders corresponding to clinical uses of vitamin K and its derivatives;

Moreover, the compounds of the present invention are also, because of their properties of inhibiting cdc25 phosphatases, capable of being used to inhibit the proliferation of microorganisms, in particular yeasts. One of the advantages of these compounds is their low toxicity on healthy cells.

At present, the Applicant has discovered in a surprising manner that the compounds corresponding to general formula (I)

(I)

in which:
A represents an (A1) radical

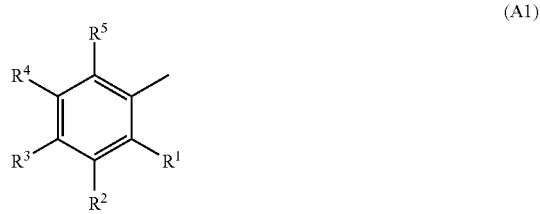
(A1)

in which two of the $R^1$, $R^2$, $R^3$, $R^4$ and $R^5$ groups represent hydrogen atoms and the other three are chosen independently from a hydrogen atom, a halogen atom and an alkyl, hydroxy, alkoxy, alkylcarbonyloxy, alkylthio or $NR^6R^7$ radical, it being understood moreover that:
either $R^1$ and one of $R^2$ and $R^4$ are chosen independently from a hydroxy, alkylcarbonyloxy and $NR^6R^7$ radical,
or $R^2$ and one of $R^3$ and $R^5$ are chosen independently from a hydroxy, alkylcarbonyloxy and $NR^6R^7$ radical,
or $R^4$ and one of $R^3$ and $R^5$ are chosen independently from a hydroxy, alkylcarbonyloxy and $NR^6R^7$ radical,
or also one of $R^1$, $R^3$ and $R^5$ is chosen from a hydroxy, alkylcarbonyloxy and $NR^6R^7$ radical, and the B—N (W)—X—Y remainder is attached to the A radical by a nitrogen atom,
$R^6$ and $R^7$ representing, independently each time that they occur, a hydrogen atom or an alkyl radical or $R^6$ and $R^7$ forming together with the nitrogen atom a heterocycle with 4 to 7 members comprising 1 to 2 heteroatoms, the members necessary to complete the heterocycle being chosen independently from the —CR$^8$R$^9$—, —O—, —S— and —NR$^{10}$— radicals, R$^8$ and R$^9$ independently representing each time that they occur a hydrogen atom or an alkyl, alkoxy, benzyloxycarbonylamino or dialkylamino radical, and R$^{10}$ independently representing each time that it occurs a hydrogen atom or an alkyl radical, or also A represents an (A2) radical

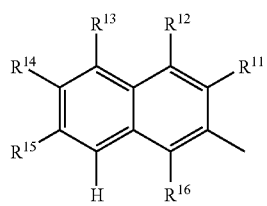

in which:
either R$^{11}$ and one of R$^{13}$, R$^{14}$ and R$^{15}$ represent hydroxy radicals whilst the other radicals among R$^{13}$, R$^{14}$ and R$^{15}$ as well as R$^{16}$ represent hydrogen atoms,
or R$^{12}$ and R$^{16}$ represent hydroxy radicals whilst R$^{11}$, R$^{13}$, R$^{14}$ and R$^{15}$ represent hydrogen atoms;

B represents a —CO—, —NH—CO—(CH$_2$)$_n$— or —(CH$_2$)$_p$— radical, n being an integer from an W represents a hydrogen atom or an alkyl radical;

X represents a —(CH$_2$)$_q$—, —(CH$_2$)$_q$—NH— or —CO—(CH$_2$)$_r$— radical, q being to 6 and r an integer from 0 to 6;

or also the B—N(W)—X—Y group is such that it represents the

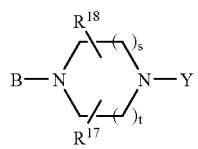

radical in which B is as defined above, t is an integer from 0 to 2, s is an integer from 0 to 1 and R$^{17}$ and R$^{18}$ represent radicals chosen independently from a hydrogen atom and an alkyl radical;

and:
when X represents a —(CH$_2$)$_q$ or —CO—(CH$_2$)$_r$— radical, then Y represents a

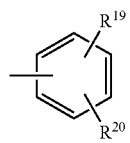

radical in which R$^{19}$ represents a hydrogen atom, a halogen atom, a nitro, alkyl, alkylthio, NR$^{21}$R$^{22}$—SO$_2$—NR$^{23}$R$^{24}$, —NH—SO$_2$—R$^{25}$ or —O—P(O)(OR$^{26}$)(OR$^{27}$) radical R$^{21}$ and R$^{22}$ independently representing a hydrogen atom or an alkyl radical, R$^{23}$ and R$^{24}$ independently representing a hydrogen atom or an alkyl radical, or also R$^{23}$ and R$^{24}$ representing together with the nitrogen atom which carries them a heterocycle with 5 to 7 members the additional members of which are chosen independently from —CHR$^{28}$—, —NR$^{29}$—, —O— and —S—, R$^{28}$ and R$^{29}$ representing, independently each time that they occur, a hydrogen atom or an alkyl radical, R$^{25}$ representing an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, hydroxy, alkoxy or nitro radicals, except for the optional nitrogen atoms of the heteroaryl nucleus for which the optional substituents are chosen from alkyl radicals, R$^{26}$ and R$^{27}$ being chosen independently from alkyl radicals, and R$^{20}$ represents a hydrogen atom, a halogen atom or an alkyl, alkoxy or alkylthio radical, or also Y represents the (T) radical represented below

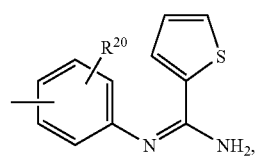

in which R$^{20}$ represents a hydrogen atom or an alkyl, alkoxy or alkylthio radical, when X represents a —(CH$_2$)$_q$—NH— radical or when the B—N(W)—X—Y group is such that it represents the

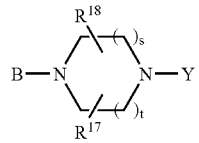

radical then Y exclusively represents an —SO$_2$—R$^{30}$ radical in which R$^{30}$ represents an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, hydroxy, alkoxy or nitro radicals, except for the optional nitrogen atoms of the heteroaryl nucleus for which the optional substituents are chosen from alkyl radicals;

it being understood moreover that when the B—N(W)—X—Y group is such that it represents the

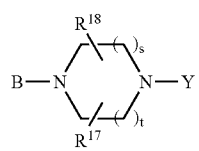

radical then B exclusively represents a —CO— or —(CH$_2$)— radical;

or the pharmaceutically acceptable salts of compounds of general formula (I) defined above are inhibitors of cdc25 phosphatases, and in particular inhibitors of cdc25-C phosphatase, and can therefore be used for preparing a medicament intended to inhibit cdc25 phosphatases, and in particular cdc25-C phosphatase.

By alkyl, unless specified otherwise, is meant a linear or branched alkyl radical containing 1 to 12 carbon atoms, preferably 1 to 10 carbon atoms and more preferentially 1 to 6 carbon atoms. By alkenyl, unless specified otherwise, is meant a linear or branched alkyl radical containing 1 to 6 carbon atoms and presenting at least one unsaturation (double bond). By alkynyl, unless specified otherwise, is meant a linear or branched alkyl radical containing 1 to 6 carbon atoms and presenting at least one double unsaturation (triple bond). By carbocyclic or heterocyclic aryl, is meant a carbocyclic or heterocyclic system comprising at least one aromatic ring, a system being said to be heterocyclic when at least one of the rings which forms it comprises a heteroatom (O, N or S); when a carbocyclic or heterocyclic aryl radical is said to be substituted unless specified otherwise, it is meant that said carbocyclic or heterocyclic aryl radical is substituted 1 to 3 times, and preferably 1 to 2 times by radicals different to a hydrogen atom which, if they are not specified, are chosen from a halogen atom and the alkyl or alkoxy radicals; moreover, unless specified otherwise, by aryl is meant a carbocyclic aryl exclusively. By haloalkyl, is meant an alkyl radical of which at least one (and optionally all) of the hydrogen atoms is replaced by a halogen atom.

By alkylthio, alkoxy, haloalkyl, haloalkoxy, aminoalkyl, alkenyl, alkynyl, aralkyl, is meant respectively the alkylthio, alkoxy, haloalkyl, haloalkoxy, aminoalkyl, alkenyl, alkynyl, aralkyl radicals the alkyl radical of which has the meaning indicated previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By carbocyclic aryl, is meant in particular the phenyl and naphthyl radicals. By heterocyclic aryl or heteroaryl, is meant in particular the thienyl, imidazolyl, thiazolyl, oxazolyl and pyridyl radicals. Finally, by halogen, is meant the fluorine, chlorine, bromine or iodine atoms.

By pharmaceutically acceptable salt, is meant in particular the addition salts with inorganic acids such as hydrochloride, hydrobromide, hydroiodide, sulphate, phosphate, diphosphate and nitrate or with organic acids such as acetate, maleate, fumarate, tartrate, succinate, citrate, lactate, methanesulphonate, p-toluenesulphonate, pamoate, and stearate. Also included in the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201–217.

In certain cases, the compounds according to the present invention can contain asymmetrical carbon atoms. As a result, the compounds according to the present invention have two possible enantiomeric forms, i.e. the "R" and "S" configurations. The present invention includes the two enantiomeric forms and all combinations of these forms, including the racemic "RS" mixtures. For the sake of simplicity, when no specific configuration is indicated in the structural formulae, it should be understood that the two enantiomeric forms and their mixtures are represented.

Preferably, the compounds of general formula (I) according to the invention will include at least one of the following characteristics:

A representing an (A1) radical

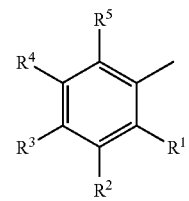

(A1)

in which two of the $R^1$, $R^2$, R, $R^4$ and $R^5$ groups represent hydrogen atoms and the other three are chosen independently from a hydrogen atom, a halogen atom and an alkyl, alkylcarbonyloxy, hydroxy, alkoxy or $NR^6R^7$ radical, it being understood moreover that:
either $R^1$ and one of $R^2$ and $R^4$ are chosen independently from a hydroxy, alkylcarbonyloxy and $NR^6R^7$ radical,
or $R^2$ and one of $R^3$ and $R^4$ are chosen independently from a hydroxy, alkylcarbonyloxy and $NR^6R^7$ radical,
or $R^4$ and one of $R^3$ and $R^5$ are chosen independently from a hydroxy, alkylcarbonyloxy and $NR^6R^7$ radical,
or also one of $R^1$, $R^3$ and $R^5$ is chosen independently from a hydroxy, alkylcarbonyloxy and $NR^6R^7$ radical, and the B—N(W)—X—Y remainder is attached to the A radical by a nitrogen atom,
$R^6$ and $R^7$ representing, independently each time that they occur, a hydrogen atom or an alkyl radical or $R^6$ and $R^7$ forming together with the nitrogen atom a heterocycle with 5 to 7 members comprising 1 to 2 heteroatoms, the members necessary to complete the heterocycle being chosen independently from the —$CR^8R^9$—, —O—, —S— and —$NR^{10}$— radicals, $R^8$ and $R^9$ independently representing each time that they occur a hydrogen atom or an alkyl or alkoxy radical, and $R^{10}$ independently representing each time that it occurs a hydrogen atom or an alkyl radical, or also A representing an (A2) radical

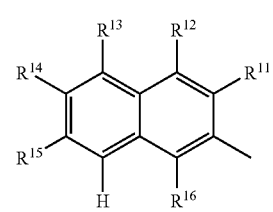

(A2)

in which:
either $R^{11}$ and one of $R^{13}$, $R^{14}$ and $R^{15}$ represent hydroxy radicals whilst the other radicals among $R^{13}$, $R^{14}$ and $R^{15}$ as well as $R^{16}$ represent hydrogen atoms,
or $R^{12}$ and $R^{16}$ represent hydroxy radicals whilst $R^{11}$, $R^{13}$, $R^{14}$ and $R^{15}$ represent hydrogen atoms;
B representing a —CO—, —NH—CO—(CH$_2$)$_n$— or —(CH$_2$)$_p$— radical, n being an integer from 0 to 2 and p being an integer from 0 to 1;

W representing a hydrogen atom or an alkyl radical;

X representing a —(CH$_2$)$_q$—, —(CH$_2$)$_q$—NH— or —CO—(CH$_2$)$_r$— radical, q being an integer from 1 to 4 and r an integer from 0 to 5;

or also the B—N(W)—X—Y group being such that it represents the

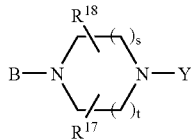

radical in which B is as defined in general formula (I), t is an integer from 0 to 2, s is an integer from 0 to 1, R$^{17}$ and R$^{18}$ represent radicals chosen independently from a hydrogen atom and an alkyl radical;

when X represents a —(CH$_2$)$_q$— or —CO—(CH$_2$)$_r$— radical, Y representing a

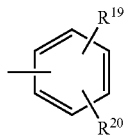

radical in which R$^{19}$ represents a hydrogen atom, a halogen atom, a nitro, alkyl, alkylthio, NR$^{21}$, R$^{22}$—SO$_2$—NR$^{23}$R$^{24}$, —NH—SO$_2$—R$^{25}$ or —O—P(O)(OR$^{26}$)(OR$^{27}$) radical, R$^{21}$ and R$^{22}$ independently representing a hydrogen atom or an alkyl radical, R$^{23}$ and R$^{24}$ independently representing a hydrogen atom or an alkyl radical, or R$^{23}$ and R$^{24}$ representing together with the nitrogen atom which carries them a heterocycle with 5 to 6 members the additional members of which are chosen independently from —CHR$^{28}$—, —NR$^{29}$—, —O— and —S—, R$^{28}$ and R$^{29}$ representing, independently each time that they occur, a hydrogen atom or an alkyl radical, R$^{25}$ representing an alkyl or aryl radical optionally substituted by one or more radicals chosen from a halogen atom and alkyl, haloalkyl, alkoxy or nitro radicals, except for the optional nitrogen atoms of the heteroaryl nucleus for which the optional substituents are chosen from alkyl radicals, R$^{26}$ and R$^{27}$ being chosen independently from alkyl radicals, and R$^{20}$ represents a hydrogen atom or an alkyl or alkoxy radical, or also Y representing the radical of formula (T)

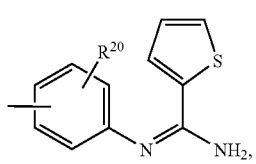

(T)

in which R$^{20}$ represents a hydrogen atom or an alkyl or alkoxy radical;

when X represents a —(CH$_2$)$_q$—NH— radical or when the B—N(W)—X—Y group is such that it represents the

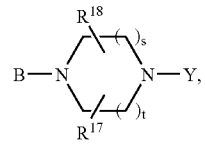

radical Y representing an —SO$_2$—R$^{30}$ radical in which R$^{30}$ represents an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, alkoxy or nitro radicals, except for the optional nitrogen atoms of the heteroaryl nucleus for which the optional substituents are chosen from alkyl radicals.

More preferentially, the compounds of general formula (I) according to the invention will include at least one of the following characteristics:

A representing an (A1) radical

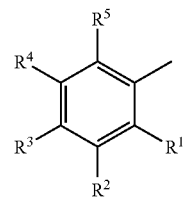

(A1)

in which two of the R$^1$, R$^2$, R$^3$, R$^4$ and R$^5$ groups represent hydrogen atoms and the other three are chosen independently from a hydrogen atom, a halogen atom and an alkyl, alkylcarbonyloxy, hydroxy, alkoxy or NR$^6$R$^7$ radical, it being understood moreover that:

either R$^1$ and one of R$^2$ and R$^4$ are chosen independently from a hydroxy, alkylcarbonyloxy and NR$^6$R$^7$ radical, or R$^2$ and one of R$^3$ and R$^4$ are chosen independently from a hydroxy, alkylcarbonyloxy and NR$^6$R$^7$ radical, or R$^4$ and one of R$^3$ and R$^4$ are chosen independently from a hydroxy, alkylcarbonyloxy and NR$^6$R$^7$ radical, or also one of R$^1$, R$^3$ and R$^5$ is chosen independently from a hydroxy, alkylcarbonyloxy and NR$^6$R$^7$ radical, and the B—N(W)—X—Y remainder is attached to the A radical by a nitrogen atom, R$^6$ and R$^7$ representing, independently each time that they occur, a hydrogen atom or an alkyl radical containing 1 to 3 carbon atoms or R$^6$ and R$^7$ forming together with the nitrogen atom a heterocycle with 5 to 6 members comprising 1 to 2 heteroatoms, the members necessary to complete the heterocycle being chosen independently from the —CR$^8$R$^9$—, —O— and —NR$^{10}$— radicals, R$^8$ and R$^9$ independently representing each time that they occur a hydrogen atom or an alkyl or alkoxy radical, and R$^{10}$ independently representing each time that it occurs a hydrogen atom or an alkyl radical, or also A representing an (A2) radical

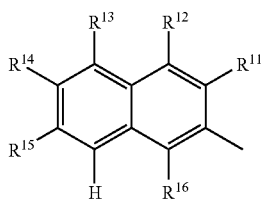

(A2)

in which:
either R[11] and R[15] represent hydroxy radicals whilst R[2], R[13], R[14] and R[16] represent hydrogen atoms,
or R[12] and R[16] represent hydroxy radicals whilst R[11], R[13], R[14] and R[15] represent hydrogen atoms;

W representing a hydrogen atom or a methyl or ethyl radical;

X representing a $-(CH_2)_q-$, $-(CH_2)_q-NH-$ or $-CO-(CH_2)_r$ radical, q being an integer from 1 to 3 and r an integer from 0 to 4;

or also the B—N(W)—X—Y group being such that it represents the

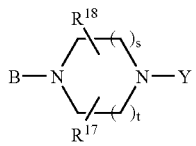

radical in which B is as defined in general formula (I), t is an integer from 0 to 2, s is an integer from 0 to 1, R[17] and R[18] represent radicals chosen independently from a hydrogen atom and an alkyl radical containing 1 to 3 carbon atoms;

when X represents a $-(CH_2)_q-$ or $-CO-(CH_2)_n-$ radical, Y representing a

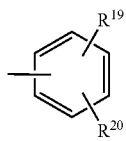

radical in which R[19] represents a nitro, NR[21]R[22], —SO₂—NR[23]R[24], —NH—SO₂—R[25] or —O—P(O)(OR[26])(OR[27]) radical, R[21] and R[22] independently representing a hydrogen atom or an alkyl radical, R[23] and R[24] independently representing a hydrogen atom or an alkyl radical, or R[23] and R[24] representing together with the nitrogen atom which carries them a heterocycle with 5 to 6 members the additional members of which are chosen independently from —CHR[28]—, —NR[29]—, —O— and —S—, R[28] and R[29] representing, independently each time that they occur, a hydrogen atom or an alkyl radical, R[25] representing an alkyl or aryl radical optionally substituted by one or more radicals chosen from a halogen atom and alkyl, haloalkyl, alkoxy or nitro radicals, except for the optional nitrogen atoms of the heteroaryl nucleus for which the optional substituents are chosen from alkyl radicals, R[26] and R[27] being chosen independently from alkyl radicals, and R[20] represents a hydrogen atom or an alkyl radical, or also Y representing the radical of formula (T)

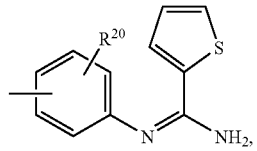

(T)

in which R[20] represents a hydrogen atom or an alkyl radical;
when X represents a $-(CH_2)_q-NH-$ radical or when the B—N(W)—X—Y group is such that it represents the

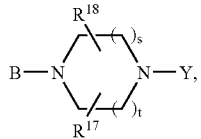

radical, Y representing an —SO₂—R[30] radical in which R[30] represents an alkyl, haloalkyl radical or one of the aryl or aralkyl radicals the aryl nucleus of which is optionally substituted by one or more radicals chosen independently from a halogen atom and alkyl, haloalkyl, alkoxy or nitro radicals, except for the optional nitrogen atoms of the heteroaryl nucleus for which the optional substituents are chosen from alkyl radicals.

Yet more preferentially, the compounds of general formula (I) according to the invention will include at least one of the following characteristics:

A representing an (A1) radical

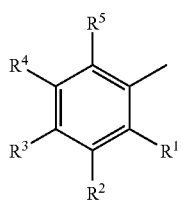

(A1)

in which two of the R[1], R[2], R[3], R[4] and R[5] groups represent hydrogen atoms and the other three are chosen independently from a hydrogen atom, a halogen atom and an alkyl, acetoxy, hydroxy, methoxy or NR[6]R[7] radical, it being understood moreover that:
either R[1] and one of R[2] and R[4] are chosen independently from a hydroxy, acetoxy and NR[6]R[7] radical,
or R[2] and one of R[3] and R[5] are chosen independently from a hydroxy, acetoxy and NR[6]R[7] radical,
or R[4] and one of R[3] and R[5] are chosen independently from a hydroxy, acetoxy and NR[6]R[7] radical, or also one of $R^1$, $R^3$ and $R^5$ is chosen independently from a hydroxy, acetoxy and $NR^6R^7$ radical, and the B—N(W)—X—Y remainder is attached to the A radical by a nitrogen atom, $R^6$ and $R^7$ representing, independently each time that they occur, a hydrogen atom or an alkyl radical containing 1 to 3 carbon atoms (this alkyl radical preferably being the methyl radical) or $R^6$ and $R^7$ forming together with the nitrogen atom a heterocycle containing 6 members and comprising 1 to 2 heteroatoms, the members necessary to complete the heterocycle being chosen independently from the —$CR^8R^9$, —O— and —$NR^{10}$— radicals, $R^8$ and $R^9$ independently representing each time that they occur a hydrogen atom or an alkyl radical (this alkyl radical preferably being the methyl radical), and $R^{10}$ independently representing each time that it occurs a hydrogen atom or an alkyl radical (this alkyl radical preferably being the methyl radical), or also A representing an (A2) radical

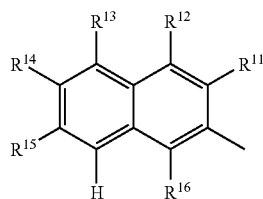

(A2)

in which $R^{11}$ and $R^{15}$ represent hydroxy radicals whilst $R^{12}$, $R^{13}$, $R^{14}$ and $R^{16}$ represent hydrogen atoms;

W representing a hydrogen atom or a methyl radical;

X representing a —$(CH_2)_q$—, $(CH_2)_q$—NH— or —CO—$(CH_2)_r$ radical, q being an integer from 1 to 3 and r an integer from 0 to 4;

or also the B—N(W)—X—Y group being such that it represents the

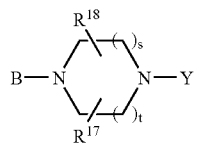

radical in which B is as defined in general formula (I), t is an integer from 0 to 2, s is an integer from 0 to 1, $R^{17}$ and $R^{18}$ represent radicals chosen independently from a hydrogen atom and a methyl radical;

when X represents a —$(CH_2)_q$— or —CO—$(CH_2)_r$— radical, Y representing a

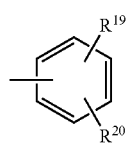

radical in which $R^{19}$ represents a nitro, $NR^{21}R^{22}$, —$SO_2$—$NR^{23}R^{24}$, —NH—$SO_2$—$R^{23}R^{24}$, —NH—$SO_2$—$R^{25}$ or —O—P(O)($OR^{26}$)($OR^{27}$) radical, $R^{21}$ and $R^{22}$ independently representing a hydrogen atom or an alkyl radical, $R^{23}$ and $R^{24}$ independently representing a hydrogen atom or an alkyl radical, or $R^{23}$ and $R^{24}$ representing together with the nitrogen atom which carries them a heterocycle with 5 to 6 members the additional members of which are chosen independently from —$CHR^{28}$—, —$NR^{29}$—, —O— and —S—, $R^{28}$ and $R^{29}$ representing, independently each time that they occur, a hydrogen atom or an alkyl radical, $R^{25}$ representing an alkyl or aryl radical optionally substituted by one or more radicals chosen from a halogen atom and alkyl, haloalkyl, alkoxy or nitro radicals, except for the optional nitrogen atoms of the heteroaryl nucleus for which the optional substituents are chosen from alkyl radicals, $R^{26}$ and $R^{27}$ being chosen independently from alkyl radicals, and $R^{20}$ represents a hydrogen atom or a methyl radical (and preferably a hydrogen atom), or also Y representing the radical of formula (T)

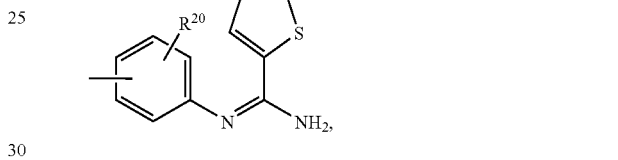

(T)

in which $R^{20}$ represents a hydrogen atom or a methyl radical (and preferably a hydrogen atom);

when X represents a —$(CH_2)_q$—NH— radical or when the B—N(W)—X—Y group is such that it represents the

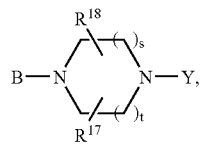

radical Y representing an —$SO_2$—$R^{30}$ radical in which $R^{30}$ represents an alkyl radical or one of the aryl or aralkyl radicals the aryl nucleus of which is optionally substituted by one or more radicals chosen independently from a halogen atom and alkyl, haloalkyl, alkoxy or nitro radicals, except for the optional nitrogen atoms of the heteroaryl nucleus for which the optional substituents are methyl radicals.

For a use according to the invention, the following compounds described (if appropriate in the form of salts) in the examples will be particularly preferred:

4-(dimethylamino)-2-methoxy-6-({methyl[2-(4-nitrophenyl)ethyl]amino} methyl)phenol;

4-(dimethylamino)-2-({methyl[2-(4-nitrophenyl)ethyl] amino}methyl)phenol;

2,7-dihydroxy-N-{2-[4-[(2-thienyl(imino)methyl)amino] phenyl]ethyl}-2-napthalenecarboxamide;

3-[(3-{[amino(2-thienyl)methylidene]amino}-benzyl) amino]-N-[4-(dimethylamino) phenyl]propanamide;

4-(4-aminophenyl)-N-[4-(4-methyl-1-piperazinyl)phenyl]butanamide;

4-(dimethylamino)-2-methoxy-6-({[2-(4-nitrophenyl)
ethyl]amino}methyl)phenol;
4-(dimethylamino)-2-({[2-(4-nitrophenyl)ethyl]
amino}methyl)phenol;
2-(dimethylamino)-6-methoxy-4-({methyl[2-(4-nitrophe-
nyl)ethyl]amino}methyl) phenol;
2-({methyl[2-(4-nitrophenyl)ethyl]amino}methyl)-1,4-
benzenediol;
4-(dimethylamino)-2-methoxy-6-({methyl[2-(4-nitrophe-
nyl)ethyl]amino}methyl)phenyl acetate;
3,7-dihydroxy-N-[2-(4-nitrophenyl)ethyl]-2-naphtha-
mide;
N-[4-(dimethylamino)benzyl]-3,7-dihydroxy-2-naphtha-
mide;
diethyl 4-{2-[(3,7-dihydroxy-2-naphthoyl)amino]
ethyl}phenylphosphate;
N-{2-[4-(aminosulphonyl)phenyl]ethyl}-3,7-dihydroxy-
2-naphthamide;
3,7-dihydroxy-N-[2-(4-aminophenyl)ethyl]-2-naphtha-
mide;
3,7-dihydroxy-N-(2-{4-[(methylsulphonyl)amino]
phenyl}ethyl)-2-naphthamide;
N-(2-{4-[(butylsulphonyl)amino]phenyl}ethyl)-3,7-dihy-
droxy-2-naphthamide;
3,7-dihydroxy-N-[2-(4-{[(4-methylphenyl)sulphonyl]
amino}phenyl)ethyl]-2-naphthamide;
3,7-dihydroxy-N-(2-{4-[(1-naphthylsulphonyl)amino]
phenyl}ethyl)-2-naphthamide;
3,7-dihydroxy-N-{2-[4-({[2-(trifluoromethyl)phenyl]
sulphonyl}amino)phenyl]ethyl}-2-naphthamide;
N-(2-{4-[(benzylsulphonyl)amino]phenyl}ethyl)-3,7-di-
hydroxy-2-naphthamide;
3,7-dihydroxy-N-{2-[4-({[3-(trifluoromethyl)phenyl]
sulphonyl}amino)phenyl]ethyl}-2-naphthamide;
3,7-dihydroxy-N-[2-(4-{[(4-nitrophenyl)sulphonyl]
amino}phenyl)ethyl]-2-naphthamide;
3,7-dihydroxy-N-{2-[4-({[4-(trifluoromethyl)phenyl]
sulphonyl}amino)phenyl]ethyl}-2-naphthamide;
3,7-dihydroxy-N-(2-{4-[(thien-2-ylsulphonyl)amino]
phenyl}ethyl)-2-naphthamide;
3,7-dihydroxy-N-[2-(4-{[(4-methoxyphenyl)sulphonyl]
amino}phenyl)ethyl]-2-naphthamide;
3,7-dihydroxy-N-[2-(4-{[(1-methyl-1 1H-imidazol-4-yl)
sulphonyl]amino}phenyl)ethyl]-2-naphthamide;
N-[2-(4-{[(4-fluorophenyl)sulphonyl]amino}phenyl)
ethyl]-3,7-dihydroxy-2-naphthamide;
3,7-dihydroxy-N-{3-[(4-methyl-1-piperidinyl)sulphonyl]
benzyl}-2-naphthamide;
5-(4-{[(1E)-amino(2-thienyl)methylidene]
amino}phenyl)-N-[2-(dimethylamino)phenyl]pentana-
mide;
3-({4-[(4-methylphenyl)sulphonyl]piperazin-1-
yl}carbonyl)naphthalene-2,6-diol;
3-{[4-(methylsulphonyl)piperazin-1-yl]
carbonyl}naphthalene-2,6-diol;
3-{[4-(butylsulphonyl)piperazin-1-yl]
carbonyl}naphthalene-2,6-diol;

or the pharmaceutically acceptable salts of such compounds.

The following compounds will quite particularly be preferred for a use according to the invention:
4-(dimethylamino)-2-methoxy-6-({methyl[2-(4-nitrophe-
nyl)ethyl]amino}methyl)phenol;
4-(dimethylamino)-2-({methyl[2-(4-nitrophenyl)ethyl]
amino}methyl)phenol;
2-(dimethylamino)-6-methoxy-4-({methyl[2-(4-nitrophe-
nyl)ethyl]amino}methyl)phenol;

2-({methyl[2-(4-nitrophenyl)ethyl]amino}methyl)-1,4-
benzenediol;
4-(dimethylamino)-2-methoxy-6-({methyl[2-(4-nitrophe-
nyl)ethyl]amino}methyl)phenyl acetate;
diethyl 4-{2-[(3,7-dihydroxy-2-naphthoyl)amino]
ethyl}phenylphosphate;
N-{2-[4-(aminosulphonyl)phenyl]ethyl}-3,7-dihydroxy-
2-naphthamide;
3,7-dihydroxy-N-(2-{4-[(methylsulphonyl)amino]
phenyl}ethyl)-2-naphthamide;
N-(2-{4-[(butylsulphonyl)amino]phenyl}ethyl)-3,7-dihy-
droxy-2-naphthamide;
3,7-dihydroxy-N-[2-(4-{[(4-methylphenyl)sulphonyl]
amino}phenyl)ethyl]-2-naphthamide;
3,7-dihydroxy-N-{2-[4-({[3-(trifluoromethyl)phenyl]
sulphonyl}amino)phenyl]ethyl}-2-naphthamide;
N-[2-(4-{[(4-fluorophenyl)sulphonyl]amino}phenyl)
ethyl]-3,7-dihydroxy-2-naphthamide;
3,7-dihydroxy-N-{3-[(4-methyl-1-piperidinyl)sulphonyl]
benzyl}-2-naphthamide;
3-({4-[(4-methylphenyl)sulphonyl]piperazin-1-
yl}carbonyl)naphthalene-2,6-diol;

or the pharmaceutically acceptable salts of such compounds.

Moreover, 5-(4-{[(1E)-amino(2-thienyl)methylidene]
amino}phenyl)-N-[2-(dimethylamino)phenyl]pentanamide
and its pharmaceutically acceptable salts are also preferred
for a use according to the invention.

The following compounds will be quite particularly preferred for a use according to the invention:
4-(dimethylamino)-2-methoxy-6-({methyl[2-(4-nitrophe-
nyl)ethyl]amino}methyl)phenol;
4-(dimethylamino)-2-({methyl[2-(4-nitrophenyl)ethyl]
amino}methyl)phenol;
2-({methyl[2-(4-nitrophenyl)ethyl]amino}methyl)-1,4-
benzenediol;
4-(dimethylamino)-2-methoxy-6-({methyl[2-(4-nitrophe-
nyl)ethyl]amino}methyl)phenyl acetate;
3,7-dihydroxy-N-{2-[4-({[3-(trifluoromethyl)phenyl]
sulphonyl}amino)phenyl]ethyl}-2-naphthamide;
3,7-dihydroxy-N-{3-[(4-methyl-1-piperidinyl)sulphonyl]
benzyl}-2-naphthamide;

or the pharmaceutically acceptable salts of such compounds.

Preferably, the compounds of general formula (I) will be used to prepare a medicament intended to treat a disease chosen from the following diseases: tumorous proliferative diseases, and in particular cancer, non-tumorous proliferative diseases, parasitic diseases, viral infections, spontaneous alopecia, alopecia induced by exogenous products and radiation-induced alopecia.

Preferably however, the compounds of general formula (I) used for preparing a medicament intended to treat proliferative diseases, parasitic diseases and viral infections are such that the Y radical does not represent the radical of formula (T). The compounds of general formula (I) in which the Y radical represents the radical of formula (T) will therefore be preferably used for preparing a medicament intended to treat spontaneous alopecia, alopecia induced by exogenous products, and radiation-induced alopecia Quite particularly, the compounds of general formula (I) could be used for preparing a medicament intended to treat cancer, and in particular cancer of the breast, lymphomas, cancers of the neck and head, cancer of the lung, cancer of the colon, cancer of the prostate and cancer of the pancreas.

According to a particular variant of the invention, the compounds of general formula (I) as defined above can be used for preparing a medicament intended to treat spontaneous alopecia, alopecia induced by exogenous products or radiation-induced alopecia.

The present invention also offers, as medicaments, the compounds of general formula (II)

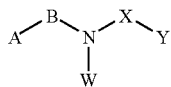
(II)

in which

A represents an (A1) radical

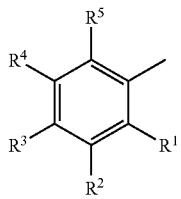
(A1)

in which two of the $R^1$, $R^2$, $R^3$, $R^4$ and $R^5$ groups represent hydrogen atoms and the other three are chosen independently from a hydrogen atom, a halogen atom and an alkyl, hydroxy, alkoxy, alkylcarbonyloxy, alkylthio or $NR^6R^7$ radical, it being understood moreover that:

either $R^1$ and one of $R^2$ and $R^4$ are chosen independently from a hydroxy, alkylcarbonyloxy and $NR^6R^7$ radical, or $R^2$ and one of $R^3$ and $R^5$ are chosen independently from a hydroxy, alkylcarbonyloxy and $NR^6R^7$ radical, or $R^4$ and one of $R^3$ and $R^5$ are chosen independently from a hydroxy, alkylcarbonyloxy and $NR^6R^7$ radical, or also one of $R^1$, $R^3$ and $R^5$ is chosen from a hydroxy, alkylcarbonyloxy and $NR^6R^7$ radical, and the B—N(W)—X—Y remainder is attached to the A radical by a nitrogen atom, $R^6$ and $R^7$ representing, independently each time that they occur, a hydrogen atom or an alkyl radical or $R^6$ and $R^7$ forming together with the nitrogen atom a heterocycle with 4 to 7 members comprising 1 to 2 heteroatoms, the members necessary to complete the heterocycle being chosen independently from the —$CR^8R^9$—, —O—, —S— and —$NR^{10}$— radicals, $R^8$ and $R^9$ independently representing each time that they occur a hydrogen atom or an alkyl, alkoxy, benzyloxycarbonylamino or dialkylamino radical, and $R^{10}$ independently representing each time that it occurs a hydrogen atom or an alkyl radical, or also A represents an (A2) radical

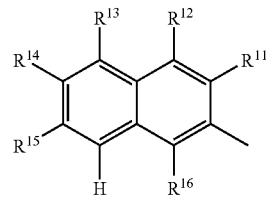
(A2)

in which:
either $R^{11}$ and one of $R^{13}$, $R^{14}$ and $R^{15}$ represent hydroxy radicals whilst the other radicals from $R^{13}$, $R^{14}$ and $R^{15}$ as well as $R^{16}$ represent hydrogen atoms, or $R^{12}$ and $R^{16}$ represent hydroxy radicals whilst $R^{11}$, $R^{13}$, $R^{14}$ and $R^{15}$ represent hydrogen atoms;

B represents a —CO—, —NH—CO—$(CH_2)_n$— or —$(CH_2)_p$— radical, n being an integer from 0 to 3 and p being an integer from 0 to 1;

W represents a hydrogen atom or an alkyl radical;

X represents a —$(CH_2)_q$—, $(CH_2)_q$—NH— or —CO—$(CH_2)_r$— radical, q being an integer from 0 to 6 and r an integer from 0 to 6;

or also the B—N(W)—X—Y group is such that it represents the

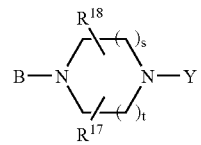

radical in which B is as defined above, t is an integer from 0 to 2, s is an integer from 0 to 1 and $R^{17}$ and $R^{18}$ represent radicals chosen independently from a hydrogen atom and an alkyl radical;

and:
when X represents a —$(CH_2)_q$— or —CO—$(CH_2)_r$— radical, then Y represents a

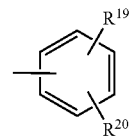

radical in which $R^{19}$ represents a hydrogen atom, a halogen atom, a nitro, alkyl, alkylthio, $NR^{21}R^{22}$, —$SO_2$—$NR^{23}R^{24}$, —NH—$SO_2$—$R^{25}$ or —O—$P(O)(OR^{26})(OR^{27})$ radical, $R^{21}$ and $R^{22}$ independently representing a hydrogen atom or an alkyl radical, $R^{23}$ and $R^{24}$ independently representing a hydrogen atom or an alkyl radical, or $R^{23}$ and $R^{24}$ representing together with the nitrogen atom which carries them a heterocycle with 5 to 7 members the additional members of which are chosen independently from —$CHR^{28}$—, —$NR^{29}$—, —O— and —S—, $R^{28}$ and $R^{29}$ representing, independently each time that they occur, a hydrogen atom or an alkyl radical, $R^{25}$ representing an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, hydroxy, alkoxy or nitro radicals, except for the optional nitrogen atoms of the heteroaryl nucleus for which the optional substituents are chosen from alkyl radicals, $R^{26}$ and $R^{27}$ being chosen independently from alkyl radicals, and $R^{20}$ represents a hydrogen atom, a halogen atom or an alkyl, alkoxy or alkylthio radical;

when X represents a —$(CH_2)_q$—NH— radical or when the B—N(W)—X—Y group is such that it represents the

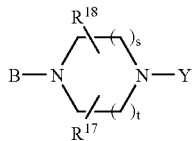

radical then Y exclusively represents an —$SO_2$—$R^{30}$ radical in which $R^{30}$ represents an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, hydroxy, alkoxy or nitro radicals, except for the optional nitrogen atoms of the heteroaryl nucleus for which the optional substituents are chosen from alkyl radicals;

it being understood moreover that when the B—N(W)—X—Y group is such that it represents the

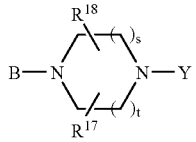

radical then B exclusively represents a —CO— or —$(CH_2)$— radical;

or the pharmaceutically acceptable salts of compounds of general formula (II).

In particular, the invention relates, as medicaments, to the following compounds of general formula (II):
  4-(dimethylamino)-2-methoxy-6-({methyl[2-(4-nitrophenyl)ethyl]amino}methyl)phenol;
  4-(dimethylamino)-2-({methyl[2-(4-nitrophenyl)ethyl]amino}methyl)phenol;
  4-(4-aminophenyl)-N-[4-(4-methyl-1-piperazinyl)phenyl]butanamide;
  4-(dimethylamino)-2-methoxy-6-({[2-(4-nitrophenyl)ethyl]amino}methyl)phenol;
  4-(dimethylamino)-2-({[2-(4-nitrophenyl)ethyl]amino}methyl)phenol;
  2-(dimethylamino)-6-methoxy-4-({methyl[2-(4-nitrophenyl)ethyl]amino}methyl)phenol;
  2-({methyl[2-(4-nitrophenyl)ethyl]amino}methyl)-1,4-benzenediol;
  4-(dimethylamino)-2-methoxy-6-({methyl[2-(4-nitrophenyl)ethyl]amino}methyl)phenyl acetate;
  3,7-dihydroxy-N-[2-(4-nitrophenyl)ethyl]-2-naphthamide;
  N-[4-(dimethylamino)benzyl]-3,7-dihydroxy-2-naphthamide;
  diethyl 4-{2-[(3,7-dihydroxy-2-naphthoyl)amino]ethyl}phenylphosphate;
  N-{2-[4-(aminosulphonyl)phenyl]ethyl}-3,7-dihydroxy-2-naphthamide;
  3,7-dihydroxy-N-[2-(4-aminophenyl)ethyl]-2-naphthamide;
  3,7-dihydroxy-N-(2-{4-[(methylsulphonyl)amino]phenyl}ethyl)-2-naphthamide;
  N-(2-{4-[(butylsulphonyl)amino]phenyl}ethyl)-3,7-dihydroxy-2-naphthamide;
  3,7-dihydroxy-N-[2-(4-{[(4-methylphenyl)sulphonyl]amino}phenyl)ethyl]-2-naphthamide;
  3,7-dihydroxy-N-(2-{4-[(1-naphthylsulphonyl)amino]phenyl}ethyl)-2-naphthamide;
  3,7-dihydroxy-N-{2-[4-({[2-(trifluoromethyl)phenyl]sulphonyl}amino)phenyl]ethyl}-2-naphthamide;
  N-(2-{4-[(benzylsulphonyl)amino]phenyl}ethyl)-3,7-dihydroxy-2-naphthamide;
  3,7-dihydroxy-N-{2-[4-({[3-(trifluoromethyl)phenyl]sulphonyl}amino)phenyl]ethyl}-2-naphthamide;
  3,7-dihydroxy-N-[2-(4-{[(4-nitrophenyl)sulphonyl]amino}phenyl)ethyl]-2-naphthamide;
  3,7-dihydroxy-N-{2-[4-({[4-(trifluoromethyl)phenyl]sulphonyl}amino) phenyl]ethyl}-2-naphthamide;
  3,7-dihydroxy-N-(2-{4-[(thien-2-ylsulphonyl)amino]phenyl}ethyl)-2-naphthamide;
  3,7-dihydroxy-N-[2-(4-{[(4-methoxyphenyl)sulphonyl]amino}phenyl)ethyl]-2-naphthamide;
  3,7-dihydroxy-N-[2-(4-{[(1-methyl-1H-imidazol-4-yl)sulphonyl]amino}phenyl)ethyl]-2-naphthamide;
  N-[2-(4-{[(4-fluorophenyl)sulphonyl]amino}phenyl)ethyl]-3,7-dihydroxy-2-naphthamide;
  3,7-dihydroxy-N-{3-[(4-methyl-1-piperidinyl)sulphonyl]benzyl}-2-naphthamide;
  3-({4-[(4-methylphenyl)sulphonyl]piperazin-1-yl}carbonyl)naphthalene-2,6-diol;
  3-{[4-(methylsulphonyl)piperazin-1-yl]carbonyl}naphthalene-2,6-diol;
  3-{[4-(butylsulphonyl)piperazin-1-yl]carbonyl}naphthalene-2,6-diol;
and their pharmaceutically acceptable salts.

Moreover, the invention also relates to 5-(4-{[(1E)-amino(2-thienyl)methylidene]amino}phenyl)-N-[2-(dimethylamino) phenyl]pentanamide or one of its pharmaceutically acceptable salts, as a medicament.

In addition, the invention relates to the pharmaceutical compositions comprising, as active ingredient, at least one of the compounds of general formula (II) defined above or a pharmaceutically acceptable salt of such a compound, and preferably a compound chosen from the following compounds:
  4-(dimethylamino)-2-methoxy-6-({methyl[2-(4-nitrophenyl)ethyl]amino}methyl)phenol;
  4-(dimethylamino)-2-({methyl[2-(4-nitrophenyl)ethyl]amino}methyl)phenol;
  4-(4-aminophenyl)-N-[4-(4-methyl-1-piperazinyl)phenyl]butanamide;
  4-(dimethylamino)-2-methoxy-6-({[2-(4-nitrophenyl)ethyl]amino}methyl)phenol;
  4-(dimethylamino)-2-({[2-(4-nitrophenyl)ethyl]amino}methyl)phenol;

2-(dimethylamino)-6-methoxy-4-({methyl[2-(4-nitrophenyl)ethyl]amino}methyl)phenol;
2-({methyl[2-(4-nitrophenyl)ethyl]amino}methyl)-1,4-benzenediol;
4-(dimethylamino)-2-methoxy-6-({methyl[2-(4-nitrophenyl)ethyl]amino}methyl)phenyl acetate;
3,7-dihydroxy-N-[2-(4-nitrophenyl)ethyl]-2-naphthamide;
N-[4-(dimethylamino)benzyl]-3,7-dihydroxy-2-naphthamide;
diethyl 4-{2-[(3,7-dihydroxy-2-naphthoyl)amino]ethyl}phenylphosphate;
N-{2-[4-(aminosulphonyl)phenyl]ethyl}-3,7-dihydroxy-2-naphthamide;
3,7-dihydroxy-N-[2-(4-aminophenyl)ethyl]-2-naphthamide;
3,7-dihydroxy-N-(2-{4-[(methylsulphonyl)amino]phenyl}ethyl)-2-naphthamide;
N-(2-{4-[(butylsulphonyl)amino]phenyl}ethyl)-3,7-dihydroxy-2-naphthamide;
3,7-dihydroxy-N-[2-(4-{[(4-methylphenyl)sulphonyl]amino}phenyl)ethyl]-2-naphthamide;
3,7-dihydroxy-N-(2-{4-[(1-naphthylsulphonyl)amino]phenyl}ethyl)-2-naphthamide;
3,7-dihydroxy-N-{2-[4-({[2-(trifluoromethyl)phenyl]sulphonyl}amino)phenyl]ethyl}-2-naphthamide;
N-(2-{4-[(benzylsulphonyl)amino]phenyl}ethyl)-3,7-dihydroxy-2-naphthamide;
3,7-dihydroxy-N-{2-[4-({[3-(trifluoromethyl)phenyl]sulphonyl}amino)phenyl]ethyl}-2-naphthamide;
3,7-dihydroxy-N-[2-(4-{[(4-nitrophenyl)sulphonyl]amino}phenyl)ethyl]-2-naphthamide;
3,7-dihydroxy-N-{2-[4-({[4-(trifluoromethyl)phenyl]sulphonyl}amino) phenyl]ethyl}-2-naphthamide;
3,7-dihydroxy-N-(2-{4-[(thien-2-ylsulphonyl)amino]phenyl}ethyl)-2-naphthamide;
3,7-dihydroxy-N-[2-(4-{[(4-methoxyphenyl)sulphonyl]amino}phenyl)ethyl]-2-naphthamide;
3,7-dihydroxy-N-[2-(4-{[(1-methyl-1H-imidazol-4-yl)sulphonyl]amino}phenyl)ethyl]-2-naphthamide;
N-[2-(4-{[(4-fluorophenyl)sulphonyl]amino}phenyl)ethyl]-3,7-dihydroxy-2-naphthamide;
3,7-dihydroxy-N-{3-[(4-methyl-1-piperidinyl)sulphonyl]benzyl}-2-naphthamide;
3-({4-[(4-methylphenyl)sulphonyl]piperazin-1-yl}carbonyl)naphthalene-2,6-diol;
3-{[4-(methylsulphonyl)piperazin-1-yl]carbonyl}naphthalene-2,6-diol;
3-{[4-(butylsulphonyl)piperazin-1-yl]carbonyl}naphthalene-2,6-diol;

and their pharmaceutically acceptable salts.

According to a variant of the invention, a pharmaceutical composition according to the invention will include 5-(4-{[(1E)-amino(2-thienyl)methylidene]amino}phenyl)-N-[2-(dimethylamino)phenyl]pentanamide or one of its pharmaceutically acceptable salts.

More preferentially, a pharmaceutical composition according to the invention will include, as active ingredient, a compound chosen from the following compounds:

4-(dimethylamino)-2-methoxy-6-({methyl[2-(4-nitrophenyl)ethyl]amino}methyl)phenol;
4-(dimethylamino)-2-({methyl[2-(4-nitrophenyl)ethyl]amino}methyl)phenol;
2-(dimethylamino)-6-methoxy-4-({methyl[2-(4-nitrophenyl)ethyl]amino}methyl)phenol;
2-({methyl[2-(4-nitrophenyl)ethyl]amino}methyl)-1,4-benzenediol;
4-(dimethylamino)-2-methoxy-6-({methyl[2-(4-nitrophenyl)ethyl]amino}methyl)phenyl acetate;
diethyl 4-{2-[(3,7-dihydroxy-2-naphthoyl)amino]ethyl}phenylphosphate;
N-{2-[4-(aminosulphonyl)phenyl]ethyl}-3,7-dihydroxy-2-naphthamide;
3,7-dihydroxy-N-(2-{4-[(methylsulphonyl)amino]phenyl}ethyl)-2-naphthamide;
N-(2-{4-[(butylsulphonyl)amino]phenyl}ethyl)-3,7-dihydroxy-2-naphthamide;
3,7-dihydroxy-N-[2-(4-{[(4-methylphenyl)sulphonyl]amino}phenyl)ethyl]2-naphthamide;
3,7-dihydroxy-N-{2-[4-({[3-(trifluoromethyl)phenyl]sulphonyl}amino)phenyl]ethyl}-2-naphthamide;
N-[2-(4-{[(4-fluorophenyl)sulphonyl]amino}phenyl)ethyl]-3,7-dihydroxy-2-naphthamide;
3,7-dihydroxy-N-{3-[(4-methyl-1-piperidinyl)sulphonyl]benzyl)-2-naphthamide;
3-({4-[(4-methylphenyl)sulphonyl]piperazin-1-yl}carbonyl)naphthalene-2,6-diol;

or a pharmaceutically acceptable salt of one of the latter.

Also more preferentially, a pharmaceutical composition according to the invention will include, as active ingredient, a compound chosen from the following compounds:

4-(dimethylamino)-2-methoxy-6-({methyl[2-(4-nitrophenyl)ethyl]amino}methyl)phenol;
4-(dimethylamino)-2-({methyl[2-(4-nitrophenyl)ethyl]amino}methyl)phenol;
2-({methyl[2-(4-nitrophenyl)ethyl]amino}methyl)-1,4-benzenediol;
4-(dimethylamino)-2-methoxy-6-({methyl[2-(4-nitrophenyl)ethyl]amino}methyl)phenyl acetate;
3,7-dihydroxy-N-{2-[4-({[3-(trifluoromethyl)phenyl]sulphonyl}amino)phenyl]ethyl}-2-naphthamide;
3,7-dihydroxy-N-{3-[(4-methyl-1-piperidinyl)sulphonyl]benzyl}-2-naphthamide;

or a pharmaceutically acceptable salt of one of the latter.

The invention relates moreover to the use of a compound of general formula (II) as defined previously for preparing a medicament intended to treat a disease chosen from the following diseases: tumorous proliferative diseases, and in particular cancer, non-tumorous proliferative diseases, parasitic diseases, viral infections, neurodegenerative diseases, myopathies, spontaneous alopecia, alopecia induced by exogenous products, radiation-induced alopecia Preferably, the compounds of general formula (II) will be used for preparing a medicament intended to treat a disease chosen from the following diseases: tumorous proliferative diseases and in particular cancer, non-tumorous proliferative diseases, parasitic diseases, viral infections, spontaneous alopecia, alopecia induced by exogenous products and radiation-induced alopecia.

Quite particularly, the compounds of general formula (II) could be used for preparing a medicament intended to treat cancer, and in particular cancer of the breast, lymphomas, cancers of the neck and head, cancer of the lung, cancer of the colon, cancer of the prostate and cancer of the pancreas.

The invention also relates, as new industrial products, to the compounds of general formula (III)

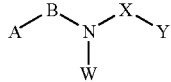 (III)

in which
A represents an (A1) radical

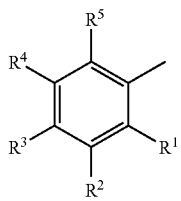 (A1)

in which two of the $R^1$, $R^2$, $R^3$, $R^4$ and $R^5$ groups represent hydrogen atoms and the other three are chosen independently from a hydrogen atom, a halogen atom and an alkyl, hydroxy, alkoxy, alkylcarbonyloxy, alkylthio or $NR^6R^7$ radical, it being understood moreover that:
  either $R^1$ and one of $R^2$ and $R^4$ are chosen independently from a hydroxy, alkylcarbonyloxy and $NR^6R^7$ radical,
  or $R^2$ and one of $R^3$ and $R^5$ are chosen independently from a hydroxy, alkylcarbonyloxy and $NR^6R^7$ radical,
  or $R^4$ and one of $R^3$ and $R^5$ are chosen independently from a hydroxy, alkylcarbonyloxy and $NR^6R^7$ radical,
  or also one of $R^1$, $R^3$ and $R^5$ is chosen from a hydroxy, alkylcarbonyloxy and $NR^6R^7$ radical, and the B—N(W)—X—Y remainder is attached to the A radical by a nitrogen atom,
$R^6$ and $R^7$ representing, independently each time that they occur, a hydrogen atom or an alkyl radical or $R^6$ and $R^7$ forming together with the nitrogen atom a heterocycle with 4 to 7 members comprising 1 to 2 heteroatoms, the members necessary to complete the heterocycle being chosen independently from the —$CR^8R^9$—, —O—, —S— and —$NR^{10}$— radicals,
$R^8$ and $R^9$ independently representing each time that they occur a hydrogen atom or an alkyl, alkoxy, benzyloxycarbonylamino or dialkylamino radical, and $R^{10}$ independently representing each time that it occurs a hydrogen atom or an alkyl radical, or also A represents an (A2) radical

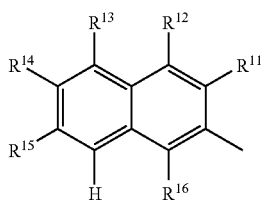 (A2)

in which:
  either $R^{11}$ and one of $R^{13}$, $R^{14}$ and $R^{15}$ represent hydroxy radicals whilst the other radicals from $R^{13}$, $R^{14}$ and $R^{15}$ as well as $R^{16}$ represent hydrogen atoms,
  or $R^{12}$ and $R^{16}$ represent hydroxy radicals whilst $R^{11}$, $R^{13}$, $R^{14}$ and $R^{15}$ represent hydrogen atoms;
B represents a —CO—, —NH—CO—$(CH_2)_n$— or —$(CH_2)_p$— radical, n being an integer from 0 to 1;
W represents a hydrogen atom or an alkyl radical;
X represents a —$(CH_2)_q$—, —$(CH_2)_q$—NH— or —CO—$(CH_2)_r$— radical, q being an integer from 1 to 6 and r an integer from 0 to 6;
or also the B—N(W)—X—Y group is such that it represents the

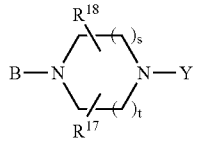

radical in which B is as defined above, t is an integer from 0 to 2, s is an integer from 0 to 1 and $R^{17}$ and $R^{18}$ represent radicals chosen independently from a hydrogen atom and an alkyl radical;

and:
  when X represents a —$(CH_2)_q$— or —CO—$(CH_2)_r$— radical, then Y represents a

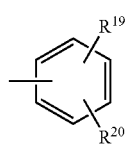

radical in which $R^{19}$ represents an —$SO_2$—$NR^{23}R^{24}$, —NH—$SO_2$—$R^{25}$ or —O—P(O)($OR^{26}$)($OR^{27}$) radical,
$R^{23}$ and $R^{24}$ independently representing a hydrogen atom or an alkyl radical, or $R^{23}$ and $R^{24}$ representing together with the nitrogen atom which carries them a heterocycle with 5 to 7 members the additional members of which are chosen independently from —$CHR^{28}$—, —$NR^{29}$—, —O— and —S—, $R^{28}$ and $R^{29}$ representing, independently each time that they occur, a hydrogen atom or an alkyl radical,
$R^{25}$ representing an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, hydroxy, alkoxy or nitro radicals, except for the optional nitrogen atoms of the heteroaryl nucleus for which the optional substituents are chosen from alkyl radicals,
$R^{26}$ and $R^{27}$ being chosen independently from alkyl radicals,
and $R^{20}$ represents a hydrogen atom, a halogen atom or an alkyl, alkoxy or alkylthio radical;
when X represents a —$(CH_2)_q$—NH— radical or when the B—N(W)—X—Y group is such that it represents the

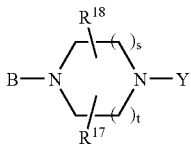

radical then Y exclusively represents an —SO$_2$—R$^{30}$ radical in which R$^{30}$ represents an alkyl, haloalkyl radical or one of the aryl, heteroaryl, aralkyl or heteroaralkyl radicals the aryl or heteroaryl nucleus of which is optionally substituted by one or more radicals chosen independently from a halogen atom and alkyl, haloalkyl, hydroxy, alkoxy or nitro radicals, except for the optional nitrogen atoms of the heteroaryl nucleus for which the optional substituents are chosen from alkyl radicals;

it being understood moreover that when the B—N(W)—X—Y group is such that it represents the

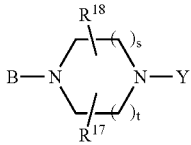

radical then B exclusively represents a —CO— or —(CH$_2$)— radical;

or the salts of compounds of general formula (III).

In particular, the invention relates, as new products, to the following compounds of general formula (III):

diethyl 4-{2-[(3,7-dihydroxy-2-naphthoyl)amino]ethyl}phenylphosphate;
N-{2-[4-(aminosulphonyl)phenyl]ethyl}-3,7-dihydroxy-2-naphthamide;
3,7-dihydroxy-N-(2-{4-[(methylsulphonyl)amino]phenyl}ethyl)-2-naphthamide;
N-(2-{4-[(butylsulphonyl)amino]phenyl}ethyl)-3,7-dihydroxy-2-naphthamide;
3,7-dihydroxy-N-[2-(4-{[(4-methylphenyl)sulphonyl]amino}phenyl)ethyl]-2-naphthamide;
3,7-dihydroxy-N-(2-{4-[(1-naphthylsulphonyl)amino]phenyl}ethyl)-2-naphthamide;
3,7-dihydroxy-N-{2-[4-({[2-(trifluoromethyl)phenyl]sulphonyl}amino)phenyl]ethyl}-2-naphthamide;
N-(2-{4-[(benzylsulphonyl)amino]phenyl}ethyl)-3,7-dihydroxy-2-naphthamide;
3,7-dihydroxy-N-{2-[4-({[3-(trifluoromethyl)phenyl]sulphonyl}amino)phenyl]ethyl}-2-naphthamide;
3,7-dihydroxy-N-[2-(4-{[(4-nitrophenyl)sulphonyl]amino}phenyl)ethyl]-2-naphthamide;
3,7-dihydroxy-N-{2-[4-({[4-(trifluoromethyl)phenyl]sulphonyl}amino) phenyl]ethyl}-2-naphthamide;
3,7-dihydroxy-N-(2-{4-[(thien-2-ylsulphonyl)amino]phenyl} ethyl)-2-naphthamide;
3,7-dihydroxy-N-[2-(4-{[(4-methoxyphenyl)sulphonyl]amino}phenyl)ethyl]-2-naphthamide;
3,7-dihydroxy-N-[2-(4-{[(1-methyl-1H-imidazol-4-yl)sulphonyl]amino}phenyl)ethyl]-2-naphthamide;
N-[2-(4-{[(4-fluorophenyl)sulphonyl]amino}phenyl)ethyl]-3,7-dihydroxy-2-naphthamide;
3,7-dihydroxy-N-{3-[(4-methyl-1-piperidinyl)sulphonyl]benzyl}-2-naphthamide;
3-({4-[(4-methylphenyl)sulphonyl]piperazin-1-yl}carbonyl)naphthalene-2,6-diol;
3-{[4-(methylsulphonyl)piperazin-1-yl]carbonyl}naphthalene-2,6-diol;
3-{[4-(butylsulphonyl)piperazin-1-yl]carbonyl}naphthalene-2,6-diol;

and the salts of the latter.

The invention also relates, as new products, to the following compounds of general formula (I):

4-(dimethylamino)-2-({methyl[2-(4-nitrophenyl)ethyl]amino}methyl)phenol;
4-(4-aminophenyl)-N-[4-(4-methyl-1-piperazinyl)phenyl]butanamide;
4-(dimethylamino)-2-methoxy-6-({[2-(4-nitrophenyl)ethyl]amino}methyl)phenol;
4-(dimethylamino)-2-({[2-(4-nitrophenyl)ethyl]amino}methyl)phenol;
2-(dimethylamino)-6-methoxy-4-({methyl[2-(4-nitrophenyl)ethyl]amino}methyl)phenol;
2-({methyl[2-(4-nitrophenyl)ethyl]amino}methyl)-1,4-benzenediol;
4-(dimethylamino)-2-methoxy-6-({methyl[2-(4-nitrophenyl)ethyl]amino}methyl)phenyl acetate;
3,7-dihydroxy-N-[2-(4-nitrophenyl)ethyl]-2-naphthamide;
N-[4-(dimethylamino)benzyl]-3,7-dihydroxy-2-naphthamide;

and the salts of the latter.

The invention also relates, as a new industrial product corresponding to general formula (I), to 5-(4-{[(1E)-amino(2-thienyl)methylidene]amino}phenyl)-N-[2-(dimethylamino)phenyl]pentanamide.

The invention also relates to pharmaceutical compositions comprising, as active ingredient, a compound of general formula (III) or a pharmaceutically acceptable salt of the latter.

Another subject of the invention is the use of compounds of general formula (III) or of pharmaceutically acceptable salts of the latter for preparing medicaments intended to treat a disease chosen from the following diseases: tumorous proliferative diseases, and in particular cancer, non-tumorous proliferative diseases, parasitic diseases, viral infections, neurodegenerative diseases, myopathies, spontaneous alopecia, alopecia induced by exogenous products, radiation-induced alopecia Preferably, the compounds of general formula (III) are used for preparing a medicament intended to treat a disease chosen from the following diseases: tumorous proliferative diseases, and in particular cancer, non-tumorous proliferative diseases, parasitic diseases, viral infections, spontaneous alopecia, alopecia induced by exogenous products, radiation-induced alopecia Quite particularly, the compounds of general formula (III) could be used for preparing a medicament intended to treat cancer, and in particular cancer of the breast, lymphomas, cancers of the neck and head, cancer of the lung, cancer of the colon, cancer of the prostate and cancer of the pancreas.

Generally, the same preferences as those indicated for the compounds of general formula (I) are moreover applicable by analogy to the compounds of general formulae (II) and (III).

The invention also relates to a process for the preparation of a compound of general formula (I).3

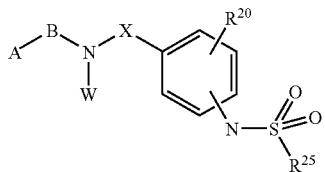
(I).3 in which A, B, W, X, $R^{20}$ and $R^{25}$ have the same meaning as in general formula (I), said process being characterized in that the compound of general formula (I).2

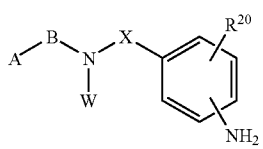
(I).2 is reacted with a compound of general formula $R^{25}$—$SO_2Cl$ in an aprotic solvent (such as tetrahydrofuran, dichloromethane or dimethylformamide) and in the presence of a base (such as pyridine, triethylamine or a supported base, for example morpholinomethyl polystyrene resin; the base being able if appropriate to also serve as reaction solvent).

The invention also relates to a process for the preparation of a compound of general formula (I).7

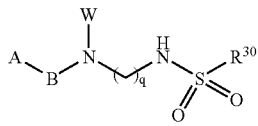
(I).7 in which A, B, W, q and $R^{30}$ have the same meaning as in general formula (I), said process being characterized in that the compound of formula (XXVII)

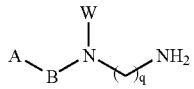
(XXVII)

is reacted with a compound of general formula

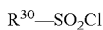 (XXVIII)

in an aprotic solvent (such as tetrahydrofuran, dichloromethane or dimethylformamide) and in the presence of a base (such as pyridine, triethylamine or a supported base, for example morpholinomethyl polystyrene resin; the base being able if appropriate to also serve as reaction solvent).

The invention also relates to a process for the preparation of a compound of general formula (I).8

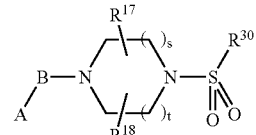
(I).8 in which A, B, $R^{17}$, $R^{18}$, s, t and $R^{30}$ have the same meaning as in general formula (I), said process being characterized in that the compound of formula (XXVII)a

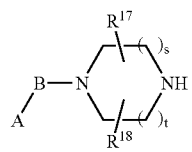
(XXII)a is reacted with a compound of general formula $R^3$—$SO_2Cl$ (XXVIII)

in an aprotic solvent (such as tetrahydrofuran, dichloromethane or dimethylformamide) and in the presence of a base (such as pyridine, triethylamine or a supported base, for example morpholinomethyl polystyrene resin; the base being able if appropriate to also serve as reaction solvent).

The invention also relates to a process for the preparation of a compound of general formula (I).9

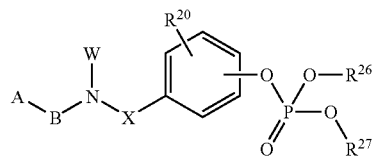
(I).9 in which A, W, X, $R^{20}$, $R^{26}$ and $R^{27}$ have the same meaning as in general formula (I), and B represents the —CO— or —$CH_2$— radical, said process being characterized in that the amine of general formula (IV)$_p$

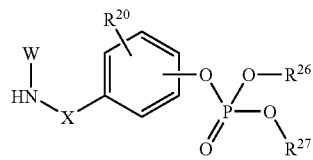
(IV)$_p$ is reacted with:
either, when B represents the —CO— radical, with an acid of general formula

A—$CO_2H$ (V)

in an aprotic solvent (such as tetrahydrofuran, dichloromethane or dimethylformamide) and in the presence of a peptide coupling agent (such as dicyclohexylcarbodiimide (DCC), 1,1'-carbonyldiimidazole (CDI) or 1-(3-dimethylaminoproyl)-3-ethylcarbodiimide)hydrochloride;

or, when B represents the —CH$_2$— radical, with an aldehyde of general formula

A—CHO      (VI)

in an alcoholic solvent (such as, for example, methanol) and in the presence of a reducing agent (such as NaBH$_4$, NaBH$_3$CN or also a resin containing borohydride ions).

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The administration of a medicament according to the invention can be carried out by topical, oral, parenteral route, by intramuscular injection, etc.

The administration dose envisaged for a medicament according to the invention is comprised between 0.1 mg and 10 g according to the type of active compound used.

In accordance with the invention, the compounds of general formula (I) can be prepared for example by the processes described below.

Preparation of the Compounds of the Invention

The preparation processes below are given by way of illustration and a person skilled in the art will be able to subject them to the variations that he judges useful, both as regards to the reagents and the conditions and techniques of the reactions.

A) Case where Y Represents a Substituted Phenyl Radical

1. Case where Y Represents a Radical of Nitrophenyl Type:

The compounds of general formula (I) in which Y represents a radical of nitrophenyl type (hereafter designated by <<compounds of general sub-formula (I).1>>) can be easily prepared according to identical or similar procedures to those described in the PCT Patent Application WO 00/17190.

2. Case where Y Represents a Radical of Aminophenyl, Dialkylaminophenyl or, Alkylsulphonylamino Type or also a Radical of Formula (T):

In the case where Y represents a radical of aminophenyl, dialkylaminophenyl, alkylsulphonylamino type or also the radical of formula (T), the compounds of general formula (I) can be prepared from nitrophenyl derivatives of general sub-formula (I).1 according to the procedures represented in Diagram 1 below.

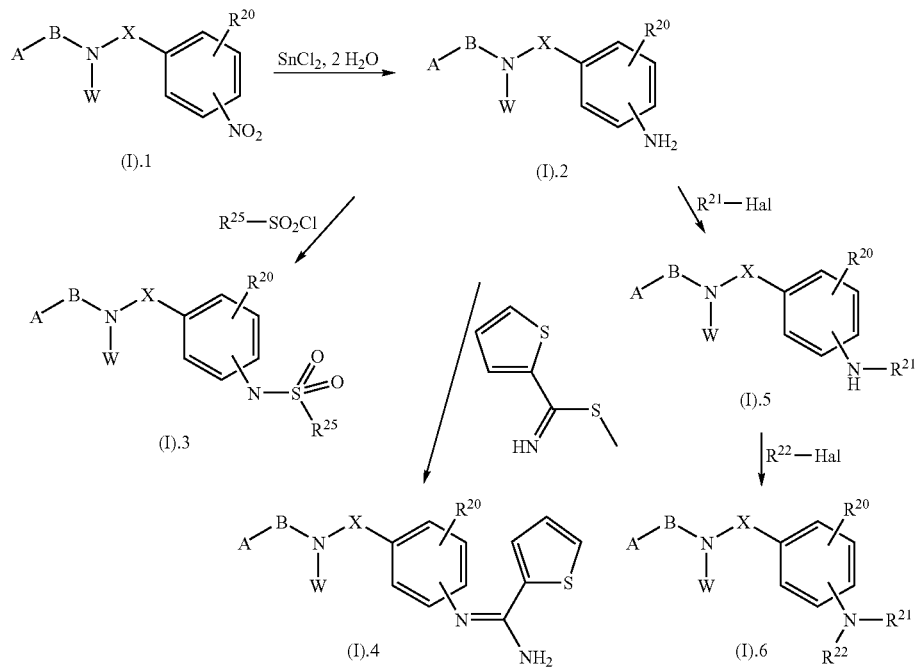

Diagram 1

In the case where neither X or B represents —CH$_2$—, the derivatives of aminophenyl type of general sub-formula (I).2, in which A, B, W, X and R$^{20}$ are as defined above can be easily obtained, Diagram 1, by reduction of the compounds of general formula (I).1, for example, by the action of hydrogen in the presence of a catalyst of the palladium on carbon type in a solvent such as for example methanol, ethanol, dichloromethane or tetrahydrofuran (THE). In the particular case where at least one of X and B represents —CH₂—, the reduction of the nitro function can be carried out, for example, by heating the product in an appropriate solvent such as ethyl acetate with a little ethanol in the presence of SnCl₂ (*J. Heterocyclic Chem.* (1987), 24, 927–930; *Tetrahedron Letters* (1984), 25(8), 839–842) or in the presence of SnCl₂/Zn (*Synthesis.* (1996), 9, 10761078using NaBH₄—BiCl₃ (*Synth. Comm.* (1995), 25(23), 3799–3803) in a solvent such as ethanol, or then by using Raney Ni with added hydrazine hydrate (*Monatshefte für Chemie*, (1995), 126, 725–732), or also by using indium in a mixture of ethanol and ammonium chloride under reflux (*Synlett* (1998), 9, 1028).

The compounds of general formula (I) in which Y represents the alkylsulphonylaminophenyl radical (i.e. the compounds of general sub-formula (I).3) can be easily prepared from the compounds of general formula (I).2, Diagram 1, according to standard methods of sulphonamide synthesis, by the action of a sulphonyl halide on an aminated derivative, in an aprotic solvent such as THF, dichloromethane or dimethylformamide (DMF), in the presence of a base such as pyridine, triethylamine or a supported base such as morpholinomethyl polystyrene resin or also by using pyridine as solvent.

The compounds of general formula (I) in which Y represents the (T) radical (i.e. the compounds of general sub-formula (I).4) can be easily prepared from the compounds of general formula (I).2, Diagram 1, according to identical or similar procedures to those described in the PCT Patent Application WO 00/17190.

Finally, the derivatives of alkylaminophenyl or dialkylaminophenyl type (the compounds of sub-general formulae (I).5 and (I).6 respectively represented in Diagram 1) can be obtained by mono- or dialkylation of the aminophenyl derivatives of general sub-formula (I).2 according to standard methods known to a person skilled in the art. Monoalkylation is carried out by reducing amination with an aldehyde or by nucleophilic substitution by reacting with an $R^{21}$-Hal halogenoalkyl equivalent in order to produce the monoalkylated derivative of general sub-formula (I).5. A second alkylation can then be carried out if appropriate by means of an $R^{22}$-Hal halogenoalkyl in order to produce the dialkylated derivative of general sub-formula (I).6.

In the particular case where $R^{21}=R^{22}=$—CH₃ and where neither X or B represents —CH₂, the nitrophenyl derivative of general sub-formula (I).2 can be treated with suitable quantities of paraformaldehyde under a hydrogen atmosphere in a solvent such as ethanol and in the presence of a catalyst of the palladium on carbon type in order to produce the dimethylaminophenyl derivative of general sub-formula (I).6a (cf. Diagram 2 below).

Diagram 2

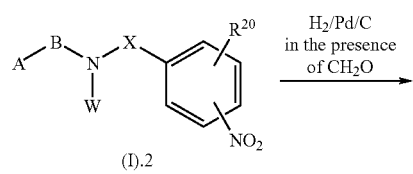

-continued

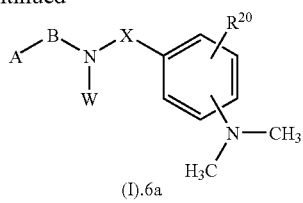

3. Other Cases where Y Represents a Radical of the Substituted Phenyl Type:

In the other cases not yet mentioned where Y represents a radical of the substituted phenyl type, the preparation of the compounds of general formula (I) will be carried out in a standard manner known to a person skilled in the art.

When the compounds of general formula (I) will include a carboxamide function (B=—CO—), they could, for example, be prepared according to methods of peptide synthesis represented in Diagram 3 below.

Diagram 3

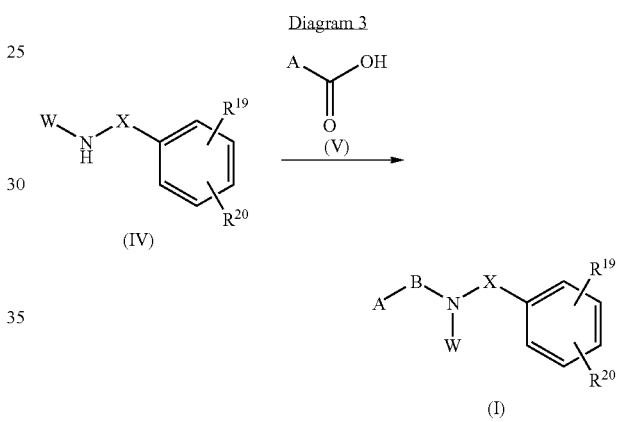

The carboxamides of general formula (I), Diagram 3, in which B represents —CO— and A, W, X, $R^{19}$ and $R^{20}$ are as defined previously, are prepared by condensation of the acids of general formula (V), with the amines of general formula (IV) under standard conditions of peptide synthesis (M. Bodanszky, The Practice of Peptide Synthesis, 145 (Springer-Verlag, 1984)), for example in THF, dichloromethane or DMF in the presence of a coupling reagent such as dicyclohexylcarbodiimide (DCC), 1,1'-carbonyldiimidazole (CDI) (*J. Med. Chem.* (1992), 35 (23), 4464–4472) or 1-(3-dimethylaminoproyl)-3-ethylcarbodiimide hydrochloride (EDC or WSCI) (John Jones, The chemical synthesis of peptides, 54 (Clarendon Press, Oxford, 1991)).

When the compounds of general formula (I) are such that B=—CH₂—, they could, for example, be prepared according to methods of reducing amination represented in Diagram 4 hereafter.

Diagram 4

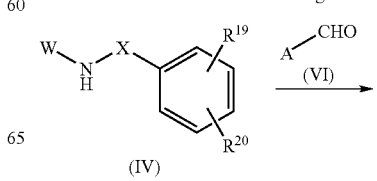

-continued

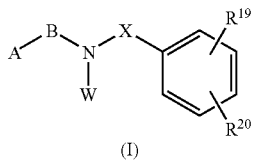

The amines of general formula (I), Diagram 4, in which B represents —CH$_2$— and A, W, X, R$_{19}$ and R$_{20}$ are as defined previously, are prepared by reaction of the aldehydes of general formula (VI) with amines of general formula (IV) in reducing medium. The reaction takes place in an alcoholic solvent such as, for example, methanol, and leads to the imine which is then converted to amine by a reducing agent such as NaBH$_4$ or NaBH$_3$CN or also an Amberlite® IRA-400 borohydride resin (Aldrich; 2.5 mmol BH$_4^-$/g of resin).

When the compounds of general formula (I) are such that B=—NH—CO—(CH$_2$)$_n$—, they could, for example, be prepared according to the synthesis methods represented in Diagram 5 below.

such as, for example, a carbamate group, under standard conditions of peptide synthesis as described above. The amine function is then deprotected (deprotection in acid medium in the case where Gp represents a carbamate group such as, for example, the tert-butoxycarbonyl group).

When the compounds of general formula (I) are such that B=—(CH$_2$)$_p$— with p=0 (in other words, B represents a bond) and X=—CO—(CH$_2$)$_r$—, they could, for example, be prepared according to the methods of peptide synthesis represented in Diagram 6 below.

Diagram 6

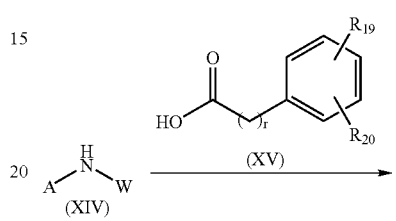

Diagram 5

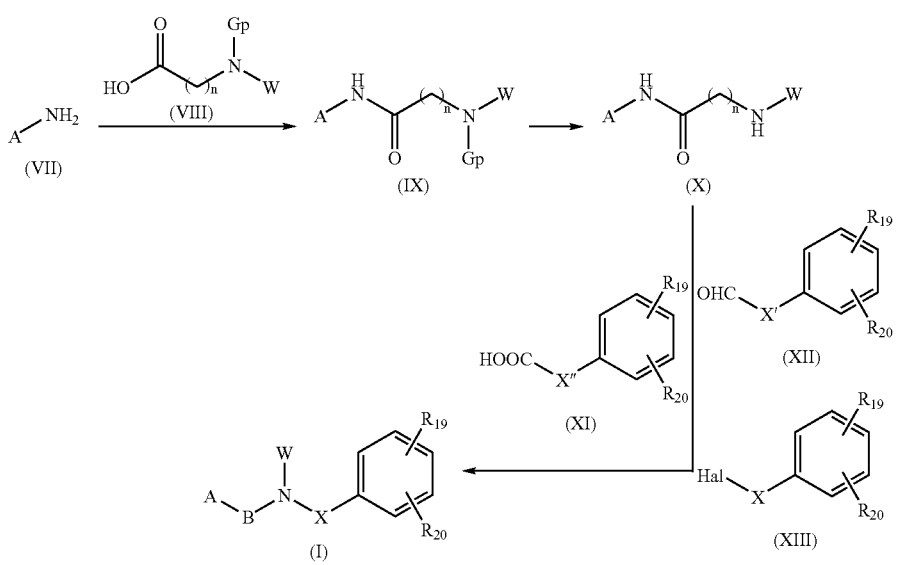

The compounds of general formula (I), Diagram 5, in which B represents —NH—CO—(CH$^2$)$_n$— and A, W, X, R$^{19}$, R$^{20}$ and n are as defined previously, are prepared by reacting amines of general formula (X) with carboxylic acids of general formula (XI) (in which X" is such that X"—CO=X) according to methods of peptide synthesis described above or also by reacting the same amines of general formula (X) with aldehydes of general formula (XII) (in which X' is such that X'—CH$_2$=X) under the conditions of reducing amination described above, or also by reacting the same amines of general formula (X) with halogenated derivatives of general formula (XIII) according to standard methods known to a person skilled in the art. The amines of general formula (X) are obtained by condensation of the amines of general formula (VII) with acids of general formula (VIII) in which A, W and n are as defined previously and Gp represents a protective group of the amine function -continued

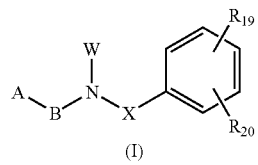

The carboxamides of general formula (I), Diagram 6, in which B represents —(CH$_2$)$_n$— with p=0, X represents —CO—(CH$_2$)$_r$— and A, W, R$^{19}$, R$^{20}$ and r are as defined previously, are prepared by condensation of the acids of general formula (XV), with the amines of general formula (XIV) under standard conditions of peptide synthesis described above.

When the compounds of general formula (I) are such that B=—(CH$_2$)$_p$— with p=0 (in other words, B represents a bond) and X=—(CH$_2$)$_q$—, they could, for example, be prepared according to the synthesis methods represented in Diagram 7 below.

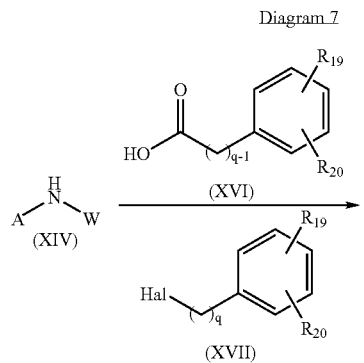

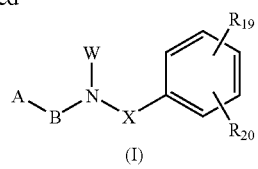

The compounds of general formula (I), Diagram 7, in which B represents —(CH$_2$)$_p$— with p=0, X represents —(CH$_2$)$_q$—, A, W, R$^{19}$, R$^{20}$ and q are as defined previously, are prepared by reaction of the amines of general formula (XIV) with aldehydes of general formula (XVI) under the conditions of reducing amination described above, or by reaction of the same amines of general formula (XIV) with halogenated derivatives of general formula (XVII) according to standard methods known to a person skilled in the art.

4. Preparation of the Amines of General Formula (IV):

The amines which are not commercially available of general formula (IV) in which X represents (CH$_2$)$_q$—, W represents H and R$^{19}$ represents an —SO$_2$—NR$^{23}$R$^{24}$ radical (hereafter designated by amines of general formula (IV)$_s$), can in particular be obtained in 6 stages according to methods in the literature, and in particular according to the method represented in Diagram 8 below.

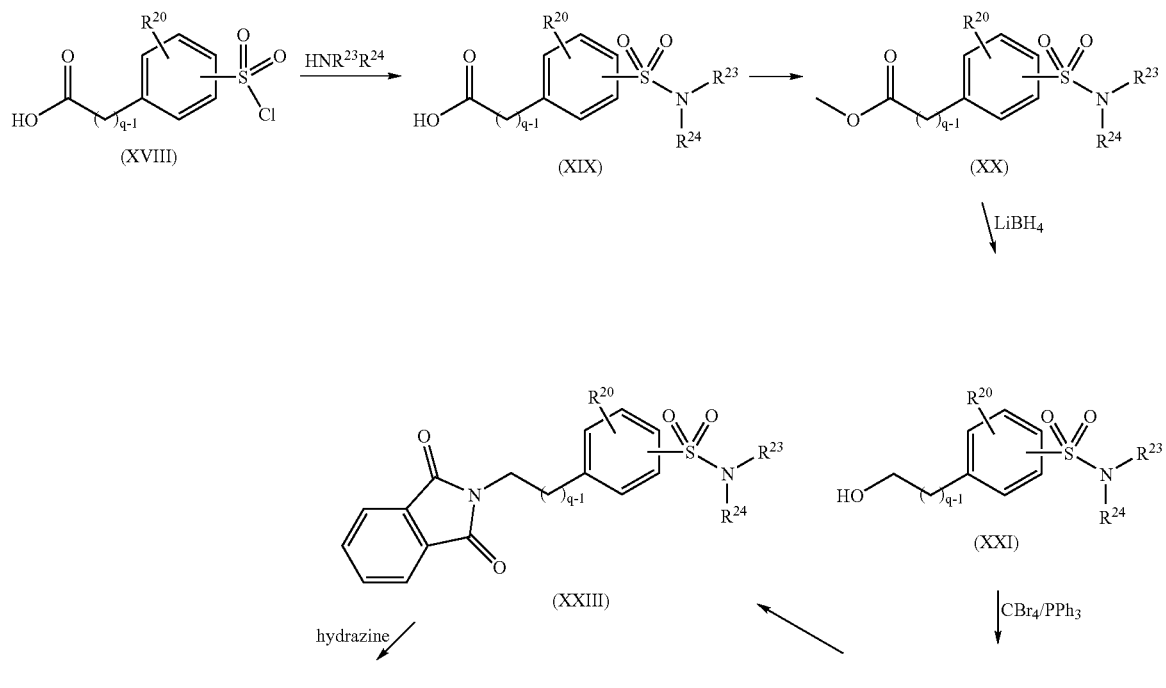

For example, Diagram 8, the alcohol of general formula (XXI) is obtained in 3 stages from the acid of general formula (XVIII), via sulphonamide by the action of a primary or secondary amine on sulphonyl chloride under the conditions described previously for the synthesis of sulphonamides, followed by esterification, for example by a treatment with trimethylsilyldiazomethane in an alcoholic solvent such as, for example, methanol, and reduction of the ester function by a reducing agent such as $LiBH_4$ in a polar aprotic solvent such as, for example, THF. The alcohol function is then halogenated by $CBr_4$ in the presence of triphenylphosphine, then converted to phthalimide by treatment of potassium phthalimidate in a polar solvent such as, for example, acetonitrile. After cleavage of the phthalimide by addition of hydrazine hydrate in an alcoholic solvent such as, for example, ethanol, the amine of general formula $(IV)_s$ is obtained.

The amines of general formula (IV) in which $R^{19}$ represents the $—O—P(O)(OR^{26})(OR^{27})$ group (hereafter designated by amines of general formula $(IV)_p$) can be obtained in 2 stages according to methods in the literature, and in particular, when X represents a $—(CH_2)_q—$ radical, according to the method represented in Diagram 9 below.

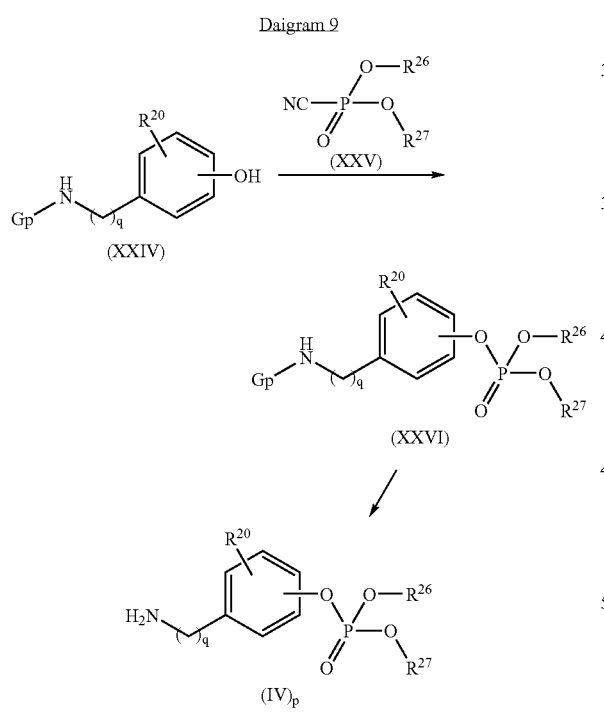

Daigram 9

According to said method, the phenol of general formula (XXIV) is substituted, Diagram 9, using a derivative of phosphonate type, in particular the cyanophosphonate of general formula (XXV), in the presence of a base such as, for example, triethylamine in a solvent such as dichloromethane. The protective group of the amine function (Gp) of the compound of formula (XXVI) is then cleaved under suitable conditions (for example in acid medium in the case where Gp is a group of carbamate type, such as the tert-butoxycarbonyl group) in order to finally produce the amine of general formula $(IV)_p$.

For the other amines of general formula (IV), a person skilled in the art could for example refer to the PCT Patent Application WO 00/17190.

5. Preparation of Certain Starting Reagents:

Certain starting reagents are not commercially available and should be prepared according to methods described in the literature. By way of example, the preparation of dihydroxy-2-naphthoic acids (A=naphthyl nucleus) can be carried out according to the methods described in Marsilje et al., *Bioorg. Med. Chem. Lett.* (2000), 10, 477–481.

The starting reagents in which A represents the phenyl radical substituted by a alkylcarbonyloxy group are obtained from corresponding phenols by the action of a corresponding acid chloride in the presence of a base such as, for example, diisopropylethylamine in a solvent such as dichloromethane.

The preparation of certain starting reagents will sometimes require the use of protection and deprotection reactions well known to a person skilled in the art who can refer, if necessary, to the following work: T. W. Greene and P. G. M. Wuts, Protective Groups in Organic Synthesis, Second edition (Wiley-Interscience, 1991), B) Case where Y Represents an $—SO_2R^{30}$ Radical:

The compounds of general formula (I) in which Y represents the $—SO_2—R^{30}$ radical (i.e. the compounds of general sub-formula (I).7 in which X represents the $—(CH_2)_q—NH—$ radical defined previously and the compounds of general sub-formula (I).8 in which the $—N(W)—X—$ group represents an optionally substituted piperazinyl nucleus) can easily be prepared from the amines of general formulae (XXVII) and (XXVII)a (in which A, B, W, $R^{17}$, $R^{18}$, q, s and t have the same meaning as in general formula (I)) according to procedures of sulphonamide synthesis as described above (cf. Diagram 10 below).

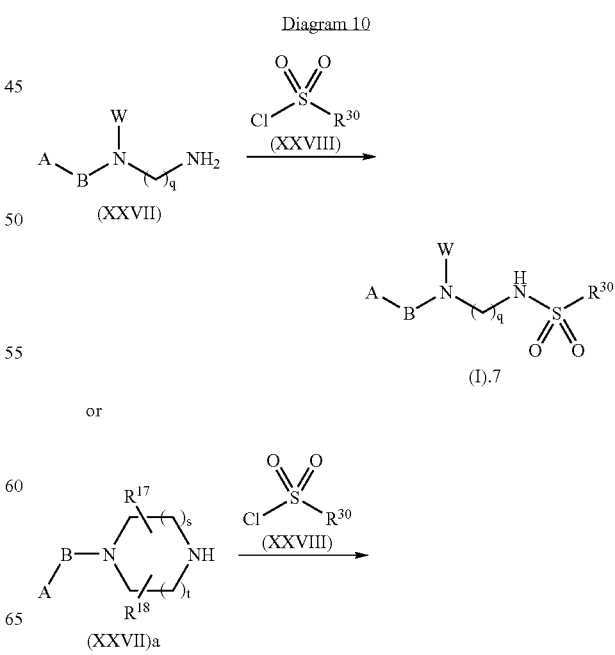

Diagram 10

-continued

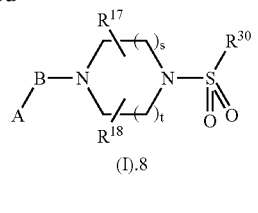

(I).8

Preparation of the Amines of General Formula (XXVII) and (XXVII)a:

When B represents —CO— or —(CH$_2$)$_p$— with p=1, the amines of general formula (XXVII) and (XXVII)a could, for example, be prepared by the procedures represented in Diagram 11 below.

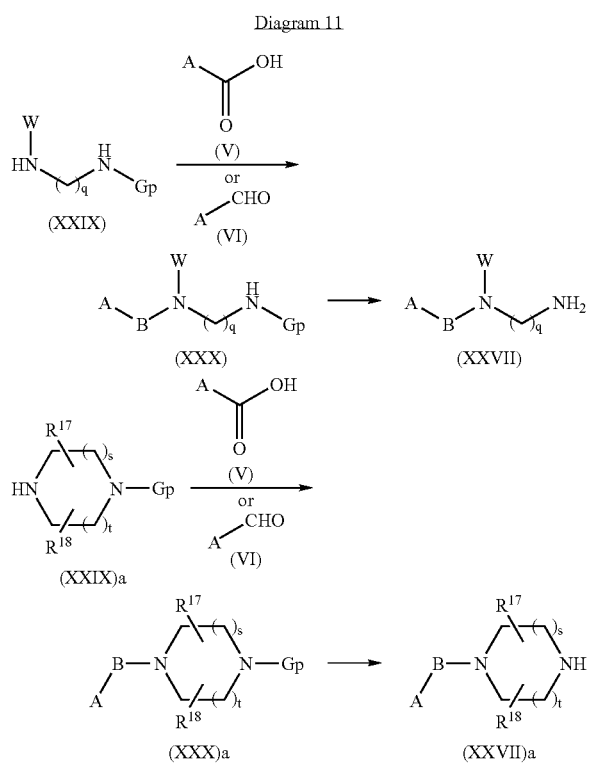

The amines which are not commercially available of general formula (XXVII) or (XXVII)a in which A, B, W, R$^{17}$, R$^{18}$, s, t and q are as defined previously are obtained by standard methods by condensation of carboxylic acids of general formula (V) and aldehydes of general formula (VI) with linear diamines of general formula (XXIX) or cyclic diamines of general formula (XXIX)a, Diagram 11, according to methods similar to those described above and in which the protective group Gp of the amine can be a carbamate group such as the tert-butoxycarbonyl group. Cleavage of the protective group is carried out according to known methods, such as for example cleavage in hydrochloric acid medium in the case of the tert-butoxycarbonyl group.

When the amines of general formula (XXVII) are such that B=—(CH$_2$)$_p$— with p=0 (in other words, B represents a bond), they could, for example, be prepared according to the synthesis methods represented in Diagram 12 below.

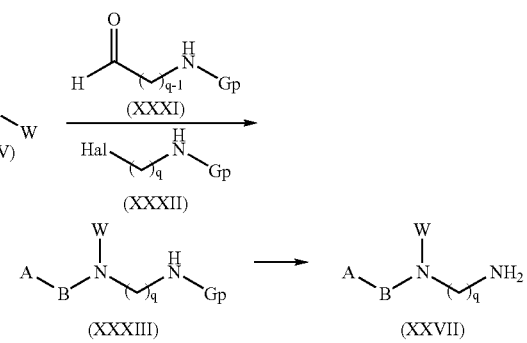

The amines of general formula (XXVII), Diagram 12, in which B represents —(CH$_2$)$_p$— with p=0, X represents —(CH$_2$)$_q$—, A, W and q are as defined previously and Gp is a protective group for an amine function (for example a protective group of carbamate type such as the tert-butoxycarbonyl group), are prepared by reacting the amines of general formula (XIV) with aldehydes of general formula (XXXI) under the conditions of reducing amination described above, or by reacting the same amines of general formula (XIV) with halogenated derivatives of general formula (XXXII) according to standard methods known to a person skilled in the art, followed by a deprotection stage of the intermediate of general formula (XXXIII) carried out under standard conditions known to a person skilled in the art.

Unless defined otherwise, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no case be considered as a limit to the scope of the invention.

EXAMPLES

Characterisation of Certain Compounds by their Retention Time r.t.

When a retention time r.t. is indicated for the compounds of the examples, this was measured by high performance liquid chromatography combined with mass spectrometry (HPLC-MS) using, according to what is indicated, the following elution conditions:

conditions I: passage from an acetonitrile-water-trifluoroacetic acid 0-1000-0.2 (A) mixture to an acetonitrile-water-trifluoroacetic acid 850-150-0.2 (B) mixture by a linear gradient over a period of 6 minutes then elution with the pure mixture B for 2 minutes.

conditions II: passage from an acetonitrile-water-trifluoroacetic acid mixture 100-900-0.2 (A) to an acetonitrile-water-trifluoroacetic acid mixture 850-150-0.2 (B) by a linear gradient over a period of 6 minutes then elution with the pure mixture B for 2 minutes.

conditions III: passage from an acetonitrile-water-trifluoroacetic acid mixture 50-950-0.2 (A) to an acetonitrile-water-trifluoroacetic acid mixture 900-100-0.2 (B) by a linear gradient over a period of 8.5 min then elution with the pure mixture B for 2 minutes.

conditions IV: passage from an acetonitrile-water-trifluoroacetic acid mixture 50-950-0.2 (A) to an acetonitrile-water-trifluoroacetic acid mixture 950-50-0 (B) by a linear gradient over a period of 8.5 minutes then elution with the pure mixture B for 10.5 minutes.

Example 1

4-(dimethylamino)-2-methoxy-6-({methyl[2-(4-nitrophenyl)ethyl]-amino}methyl)phenol It is a synthesis intermediate obtained during the preparation of the compound of Example 80 of the Application WO 00/17190, N'-(4-{2-[[5-(dimethylamino)-2-hydroxy-3-methoxybenzyl]-(methyl)amino]ethyl}-phenyl)-2-thiophenecarboximidamide, according to the procedure described in this document.

Melting point: 91–93° C.

MH+=360.30; r.t.=3.40 min (elution conditions I).

Example 2

4-(dimethylamino)-2-({methyl[2-(4-nitrophenyl)ethyl]amino}methyl)phenol 0.5 g (3 mmol) of 5-(dimethylamino)-2-hydroxybenzaldehyde (*Bull. Chem. Soc. Jpn.* (1978), 51 (8), 2433–2434) and 0.72 g (3.33 mmol) of N-methyl2-(4-nitrophenyl)ethylamine hydrochloride are placed in solution in 30 ml of anhydrous methanol under an inert atmosphere in the presence of 0.65 ml of triethylamine (4.5 mmol). The reaction mixture is stirred vigorously for 18 hours before the addition, by portions, of 126 mg (3.33 mmol) of NaBH$_4$. Stirring is maintained for a further 4 hours before adding 10 ml of ice-cold water. The reaction mixture is extracted twice with 50 ml of CH$_2$Cl$_2$. The organic phase is washed with 10 ml of water, dried over sodium sulphate, filtered and concentrated under vacuum. The residue is purified on a silica column (eluent: CH$_2$Cl$_2$/MeOH: 97/3). The expected product is obtained in the form of a brown oil with a yield of 34% (0.34 g).

NMR $^1$H (DMSO d6, 200 MHz, δ): 2.23 (s, 3H, CH$_3$); 2.71–2.77 (m, 8H, 2CH$_3$, CH$_2$); 2.96 (t, 3H, CH$_2$); 3.6 (s, 2H, CH$_2$); 6.48–6.53 (m, aromatic 3H's); 7.50–7.55 m, aromatic 2H's); 8.13–8.17 (m, aromatic 2H's).

MH+=330.31; r.t.=3.20 min (elution conditions I).

Example 3

2,7-dihydroxy-N-{2-[4-[(2-thienyl(imino)methyl)amino]phenyl]ethyl}-2-naphthalenecarboxamide hydrochloride

[It is the compound of Example 11 of the Application WO 00/17190]

Example 4

3-[(3-{[amino(2-thienyl)methylidene]amino}-benzyl)amino]-N-[4-(dimethylamino)phenyl]propanamide hydrochloride

[It is the compound of Example 50 of the Application WO 00/17190]

Example 5

4-(4-aminophenyl)-N-[4-(4-methyl-1-piperazinyl)phenyl]butanamide hydrochloride 5.1) 4-(4-nitrophenyl)-N-[4-(4-methyl-1-piperazinyl)phenyl]butanamide:

4-(N-methylpiperazinyl)aniline (0.5 g; 2.6 mmol), hydroxybenzotriazole (0.39 g; 2.86 mmol), 1-(3-dimethylaminopropyl)-3-ethyl-carbodiimide hydrochloride (1.1 g; 5.7 mmol) and triethylamine (0.8 ml; 5.7 mmol) are added to a solution of 0.55 g (2.6 mmol) of 4-(4-nitrophenyl)butanoic acid in dichloromethane (30 ml). The reaction medium is stirred for 16 hours at ambient temperature, then the medium is diluted with 15 ml of water and the product is extracted with dichloromethane. The organic phase is dried over sodium sulphate followed by filtering and concentrating under vacuum and the residue is purified on a silica column (eluent: CH$_2$Cl$_2$/EtOH: 4/1). A clear oil is obtained with a yield of 84% (0.84 g).

NMR $^1$H (CDCl$_3$, 100 MHz, δ): 2.0–2.3 (m, 2H, CH$_2$); 2.3–2.5 (m, 5H, CH$_2$, CH$_3$); 2.5–2.7 (m, 4H, 2 CH$_2$); 2.7–3.0 (m, 2H, CH$_2$); 3.1–3.3 (m, 4H, 2CH$_2$); 6.9 (s, 1H, NH); 6.9–7.1 (m, aromatic 2H's); 7.3–7.5 (m, aromatic 4H's); 8.1–8.3 (m, aromatic 2H's).

5.2) 4-(4-aminophenyl)-N-[4-(4-methyl-1-piperazinyl)phenyl]-butanamide hydrochloride:

0.1 g of palladium on carbon (10%) is added to a solution of 0.84 g (2.2 mmol) of intermediate 5.1 in a mixture of ethanol (150 ml) and dichloromethane (15 ml). The medium is placed under a hydrogen atmosphere under a pressure of 1.5 bars for 30 minutes. The catalyst is filtered and the solvent is evaporated under reduced pressure. The free base is obtained with a yield of 71% (0.55 g; 1.56 mmol) in the form of a white solid, then placed in solution in ice-cold ethanol (45 ml) and 4.6 ml (4.7 mmol) of a 1N solution of hydrochloric acid in ether is added. After stirring for 30 minutes at ambient temperature, the solvent is evaporated to dryness, then the residue is taken up in ether in order to provide the expected hydrochloride in the form of a clear brown solid with a yield of 97% (0.64 g). Melting point: 156–158° C.

NMR $^1$H (DMSO d6, 400 MHz, δ): 1.80–1.88 (m, 2H, CH$_2$); 2.27 (t, 2H, CH$_2$); 2.58 (t, 2H, CH$_2$); 2.78 (s, 3H, CH$_3$); 3.00–3.80 (m, 8H, 4 CH$_2$); 6.90–6.93 (m, aromatic 2H's); 7.04–7.06 (m, aromatic 2H's); 7.16–7.18 (m, aromatic 2H's); 7.47–7.49 (m, aromatic 2H's); 9.77 (s, 1H, NH).

MH+=353.23.

Example 6

4-(dimethylamino)-2-methoxy-6-({[2-(4-nitrophenyl)ethyl]amino}methyl)phenol

The experimental protocol used is the same as that described for the compound of Example 2,2-(4-nitrophenyl)ethylamine replacing N-methyl-2-(4-nitrophenyl)ethylamine and 2-hydroxy-3-methoxy-5-(dimethylamino)benzaldehyde replacing 2-hydroxy-5-(dimethylamino)benzaldehyde. A brown oil is obtained.

NMR $^1$H (CDCl$_3$, 400 MHz, δ): 2.85 (m, 6H, N(CH$_3$)$_2$); 2.97 (m, 4H, 2CH$_2$) 3.88 (s, 3H, OCH$_3$); 3.96 (s, 2H, CH$_2$); 6.06–6.07 (d, aromatic 1H); 6.36–6.37 (d, aromatic 1H); 7.36–7.37 (d, aromatic 2H's); 8.17–8.18 (d, aromatic 2H's).

MH+=346.20; r.t.=3.40 min (elution conditions I).

Example 7

4-(dimethylamino)-2-({[2-(4-nitrophenyl)ethyl]amino}methyl)phenol

The experimental protocol used is the same as that described for the compound of Example 2,2-(4-nitrophenyl)ethylamine replacing N-methyl-2-(4-nitrophenyl)ethylamine. A brown oil is obtained.

NMR $^1$H (DMSO d6, 400 MHz, δ): 2.71 (m, 6H, N(CH$_3$)$_2$); 2.75–2.89 (m, 4H, 2CH$_2$); 3.76 (s, 3H, CH$_3$); 6.55 (m, 3H, aromatic H); 7.48–7.50 (d, aromatic 2H's); 8.12–8.14 (d, aromatic 2H's).

MH+=316.26; r.t.=3.30 min (elution conditions I).

Example 8

2-(dimethylamino)-6-methoxy-4-({methyl[2-(4-nitrophenyl)ethyl]amino}methyl)phenol The experimental protocol used is the same as that described for the compound of Example 2,5-(dimethylamino)-4-hydroxy-3-methoxybenzaldehyde, *(Bull. Chem. Soc. Jpn.* (1978), 51(8), 2433–2434, replacing 5-(dimethylamino)-3-methoxy-2-hydroxybenzaldehyde. A brown oil is obtained.

NMR $^1$H (DMSO d6, 400 MHz, δ): 2.61–2.64 (m, 2H, CH$_2$); 2.71 (m, 6H, N(CH$_3$)$_2$); 2.88–2.90 (m, 2H, CH$_2$); 3.66 (s, 2H, CH$_2$); 7.14–7.17 (m, aromatic 2H's); 7.48–7.51 (m, aromatic 2H's); 8.13–8.15 (m, aromatic 2H's).

MH+=360.27; r.t.=3.30 min (elution conditions I).

Example 9

2-({methyl [2-(4-nitrophenyl)ethyl]amino}methyl)-1,4-benzenediol

The experimental protocol used is the same as that described for the compound of Example 2,2,5-dihydroxybenzaldehyde replacing 5-(dimethylamino)-3-methoxy-2-hydroxybenzaldehyde. A brown oil is obtained.

NMR $^1$H (DMSO d6, 400 MHz, δ): 2.22 (s, 3H, CH$_3$); 2.74 (t, 2H, CH$_2$); 2.95 (t, 2H, CH$_2$); 3.57 (s, 2H, CH$_2$); 6.48 (m, aromatic 3H's); 7.50–7.52 (d, aromatic 2H's); 8.13–8.15 (d, aromatic 2H's).

MH+=303.25; r.t.=3.80 min (elution conditions I).

Example 10

4-(dimethylamino)-2-methoxy-6-({methyl[2-(4-nitrophenyl)ethyl]amino}methyl)phenyl acetate 0.1 g (0.278 mmol) of 4-(dimethylamino)-2-methoxy-6-({methyl[2-(4-nitrophenyl)ethyl]-amino}methyl)phenol (compound of Example 1) are placed in solution in 5 ml of anhydrous dichloromethane in the presence of 49 µl (0.42 mmol; 1.5 eq.) of diisopropylethylamine at 0° C. 30 µl (0.42 mmol; 1.5 eq.) of acetyl chloride are added dropwise to the solution and the medium is stirred for 1 hour at ambient temperature. Then 10 ml of dichloromethane is added to the reaction medium which is then washed with 3 times 10 ml of a saturated solution of sodium chloride. The organic phase is dried over magnesium sulphate, followed by filtering and concentrating under vacuum. The residue is purified on a silica column (eluent: AcOEt/Heptane: 2/1) in order to produce a yellow oil with a yield of 60%.

NMR $^1$H (DMSO d6, 400 MHz, δ): 2.16 (m, 6H, 2N(CH$_3$)$_2$); 2.59 (t, 2H, CH$_2$); 2.80 (m, 6H, 2 CH$_3$); 2.87 (t, 2H, CH$_2$); 3.31 (s, 2H, CH$_2$); 3.71 (s, 3H, OCH$_3$); 6.11 (s, aromatic 1H); 6.27 (s, aromatic 1H); 7.48 (m, aromatic 2H's); 8.11 (m, aromatic 2H's).

MH+=402.19; r.t.=4.80 min (elution conditions I).

Example 11

3,7-dihydroxy-N-[2-(4-nitrophenyl)ethyl]-2-naphthamide

125 µl of 4-nitrophenethylamine (1 mmol), 1 ml of a 1M solution of N,N'-dicyclohexylcarbodiimide in dichloromethane and 135 mg (1 mmol) of hydroxybenzotriazole monohydrate are added successively to a solution of 204 mg (1 mmol) of 3,7-dihydroxy-2-naphthoic acid in dimethylformamide (10 ml). The reaction mixture is stirred for two hours at ambient temperature, followed by diluting with 100 ml of water and extracting twice with 30 ml of ethyl acetate. The organic phases are combined then washed successively with 100 ml of water then with 50 ml of a saturated solution of sodium chloride. The organic phase is dried over magnesium sulphate, followed by filtering and the solvent is eliminated by evaporation under reduced pressure. The residue is taken up in dichloromethane followed by filtering and drying under vacuum. 100 mg of product is obtained in the form of a yellow powder (yield of 30%). Melting point: >250° C.

MH+=353.20; r.t.=6.10 min (elution conditions I).

Example 12

N-[4-(dimethylamino)benzyl]-3,7-dihydroxy-2-naphthamide

The experimental protocol used is the same as that described for the compound of Example 11, 4-dimethylaminobenzylamine replacing 4-nitrophenethylamine. A yellow oil is obtained.

NMR-$^1$H (DMSO d6, 400 MHz, δ): 2.86 (s, 6H); 4.42 (s, 2H); 6.70 (m, 2H); 7.04–7.20 (m, 5H); 7.58 (d, 1H); 8.29 (s, 1H); 9.32 (t, 1H); 9.55 (s, 1H); 11.78 (s, 1H).

MH+=337.20; r.t.=4.20 min (elution conditions I).

Example 13 diethyl 4-{2-[(3,7-dihydroxy-2-naphthoyl)amino]ethyl}phenylphosphate 13.1) tert-butyl 2-(4-[(diethoxyphosphoryl)oxy]phenyl}ethylcarbamate:

1.2 g (5 mmol) of N-Boc tyramine, 0.9 g (5.5 mmol) of diethylcyanophosphonate and 1.4 ml (10 mmol) of triethylamine are placed in solution in 5 ml of dichloromethane at 0° C. under an argon atmosphere. The reaction mixture is stirred for 30 minutes at 0° C. followed by diluting with 25 ml of water and extracting with twice 30 ml of dichloromethane. The organic phases are combined followed by washing with 50 ml of water then 25 ml of a saturated solution of sodium chloride. The organic phase is dried over magnesium sulphate, followed by filtering and concentrating under vacuum. The expected product is obtained in the form of a clear oil with a yield of 92% (1.73 g).

13.2) diethyl 4-(2-aminoethyl)phenylphospate:

1.7 g (4.5 mmol) of intermediate 13.1 is dissolved in 20 ml of a 4M solution of hydrochloric acid in dioxane. The reaction mixture is stirred for 1 hour at ambient temperature then concentrated under reduced pressure. 20 ml of a saturated solution of sodium hydrogen carbonate is added to the reaction mixture which is then extracted twice with 25 ml of ethyl acetate. The desired compound is obtained with a yield of 62% (0.76 g) and is used in the following stage without other purification.

13.3) diethyl 4-(2-[(3,7-dihydroxy-2-naphthoyl)amino] ethyl}phenylphosphate:

The experimental protocol used is the same as that described for the compound of Example 11, intermediate 13.2 replacing 4-nitrophenethylamine. A yellow powder is obtained. Melting point: 192–194° C.

MH+=460.20; r.t.=9.60 min (elution conditions I).

Example 14

N-{2-[4-(aminosulphonyl)phenyl]ethyl}-3,7-dihydroxy-2-naphthamide

The experimental protocol used is the same as that described for the compound of Example 11, 4-(2-aminoethyl)benzenesulphonamide replacing 4-nitrophenethylamine. A yellow oil is obtained.

NMR-$^1$H (DMSO d6, 400 MHz, δ): 2.98 (t, 2H); 3.59 (q, 2H); 7.05–7.09 (m, 2H); 7.14 (s, 1H); 7.28 (s, 2H); 7.46 (d, 2H); 7.58 (d, 1H); 7.75 (d, 2H); 8.22 (s, 1H); 9.03 (t,1H); 9.55 (s, 1H); 11.64 (s, 1H).

MH+=387.10; r.t.=4.30 min (elution conditions I).

Example 15

3,7-dihydroxy-N-[2-(4-aminophenyl)ethyl]-2-naphthamide

It is a synthesis intermediate from obtained during the preparation of the compound of Example 11 of the Application WO 00/17190, 2,7-dihydroxy-N-{2-[4-[(2-thienyl (imino)methyl)amino]phenyl]ethyl}-2-naphthalenecarboxamide, according to the procedure described in this document. A beige solid is obtained.

MH+=323.20; r.t.=4.00 min (elution conditions I).

Example 16

3,7-dihydroxy-N-(2-{4-[(methylsulphonyl)amino] phenyl}ethyl)-2-naphthamide

44 μl (0.55 mmol) of methanesulphonyl chloride is added to a solution of 170 mg (0.5 mmol) of the compound of Example 15 in pyridine (1 ml). The reaction medium is stirred for 16 hours at ambient temperature then diluted with 20 ml of water and extracted twice with 30 ml of ethyl acetate. The organic phases are combined followed by washing successively with 20 ml of water then 20 ml of a saturated solution of sodium chloride. The organic phase is dried over magnesium sulphate, followed by filtering and the solvent is eliminated by evaporation under reduced pressure. The residue is eluted on silica with a mixture of ethyl acetate and dichloromethane (30/70). 65 mg of product is obtained (yield of 30%) in the form of a yellow powder. Melting point: 176–178° C.

MH+=401.10; r.t.=4.60 min (elution conditions II).

The Compounds of Examples 17 to 28 are Synthesized According to the Same Strategy as that Used for the Compound of Example 16.

Example 17

N-(2-{4-[(butylsulphonyl)amino]phenyl}ethyl)-3,7-dihydroxy-2-naphthamide

Yellow powder. Melting point: 193–195° C.
MH+=443.20; r.t.=5.50 min (elution conditions II).

Example 18

3,7-dihydroxy-N-[2-(4-{[(4-methylphenyl)sulphonyl]amino}phenyl) ethyl]-2-naphthamide Yellow powder. Melting point: 182–184° C.
MH+=477.20; r.t.=5.70 min (elution conditions II).

Example 19

3,7-dihydroxy-N-(2-{4-[(1-naphthylsulphonyl) amino]phenyl}ethyl)-2-naphthamide

Yellow oil.
MH+=513.20; r.t.=9.70 min (elution conditions III).

Example 20

3,7-dihydroxy-N-{2-[4-({[2-(trifluoromethyl)phenyl]sulphonyl}amino)phenyl]ethyl}-2-naphthamide Yellow oil.
MH+=531.20; r.t.=9.60 min (elution conditions III).

Example 21

N-(2-{4-[(benzylsulphonyl)amino]phenyl}ethyl)-3, 7-dihydroxy2-naphthamide

Yellow oil.
MH+=477.20; r.t.=9.20 min (elution conditions III).

Example 22

3,7-dihydroxy-N-{2-[4-({[3-(trifluoromethyl)phenyl]sulphonyl}amino)phenyl]ethyl}-2-naphthamide Brown oil.
MH+=531.20; r.t.=9.80 min (elution conditions III).

Example 23

3,7-dihydroxy-N-[2-(4-{[(4-nitrophenyl)sulphonyl] amino}phenyl) ethyl]-2-naphthamide Orange-coloured oil.
MH+=508.20; r.t.=9.30 min (elution conditions III).

Example 24

3,7-dihydroxy-N-{2-[4-({[4-(trifluoromethyl)phenyl]sulphonyl}amino)phenyl]ethyl}-2-naphthamide Brown oil.
MH+=531.20; r.t.=9.80 min (elution conditions III).

Example 25

3,7-dihydroxy-N-(2-{4-[(thien-2-ylsulphonyl)amino]phenyl}ethyl)-2-naphthamide

Yellow oil.
MH+=469.20; r.t.=9.00 min (elution conditions III).

Example 26

3,7-dihydroxy-N-[2-(4-{[(4-methoxyphenyl)sulphonyl]amino}phenyl) ethyl]-2-naphthamide Yellow oil.
MH+=493.20; r.t.=9.10 min (elution conditions III).

Example 27

3,7-dihydroxy-N-[2-(4-{[(1-methyl-1H-imidazol-4-yl)sulphonyl]amino}phenyl)ethyl]-2-naphthamide Yellow oil.
MH+=467.20; r.t.=7.90 min (elution conditions III).

Example 28

N-[2-(4-{[(4-fluorophenyl)sulphonyl]amino}phenyl) ethyl]-3,7-dihydroxy-2-naphthamide Yellow oil.
MH+=481.20; r.t.=9.20 min (elution conditions III).

Example 29

3,7-dihydroxy-N-{3-[(4-methyl-1-piperidinyl)sulphonyl]benzyl}-2-naphthamide 29.1) 3-(4-methylpiperidinosulphonyl)phenylmethanol:

11 g (50 mmol) of 3-chlorosulphonylbenzoic acid in suspension in dichloromethane (300 ml) is treated with 12.4 g (125 mmol) of 4-methylpiperidine and the reaction mixture is maintained under stirring at ambient temperature overnight. The resulting solution is washed successively with a 10% aqueous solution of citric acid and a saturated solution of sodium chloride, followed by drying ($Na_2SO_4$) and concentrating under reduced pressure in order to produce a colourless viscous residue. The latter is taken up in methanol and, whilst maintaining the temperature between 0° C. and 10° C., is titrated by trimethylsilyldiazomethane until a characteristic yellow coloration persists. The excess reagent is destroyed with a few drops of formic acid, and the reaction medium is concentrated under reduced pressure. The traces of acid and methanol are eliminated by two azeotropic evaporations under reduced pressure with toluene. The residue, taken up in tetrahydrofuran (300 ml), is treated with lithium borohydride (2N in THF, 30 ml). The reaction medium is taken to reflux for 2 hours then cooled down and hydrolyzed with a saturated solution of ammonium chloride. The resulting mixture is extracted with ethyl acetate then the organic phase is washed with a saturated solution of sodium chloride, followed by drying ($Na_2SO_4$) and concentrating under reduced pressure. The residue is purified on a silica column (eluent: 5% acetone in dichloromethane) in order to produce the expected benzyl alcohol in the form of a white solid.

NMR $^1$H (DMSO d6, 400 MHz, δ): 0.84 (d, 3H); 1.13 (m, 2H); 1.26 (m, 1H); 1.63 (d, 2H); 2.17 (t, 2H); 3.59 (d, 2H); 4.59 (d, 2H); 5.42 (t, 1H); 7.60 (m,3H); 7.67 (s, 1H).

29.2) 2-[3-(4-methylpiperidinosulphonyl)benzyl]-1,3-isoindolinedione:

950 mg (3.5 mmol) of benzyl alcohol, 1.5 equivalents of triphenylphosphine and 1.5 equivalents of phthalimide in solution in dichloromethane (50 ml) are treated with 1.5 equivalents of diisopropyl diazadicarboxylate and the reaction mixture is stirred overnight at ambient temperature, then treated with a saturated solution of ammonium chloride, washed with a saturated solution of sodium chloride, followed by drying ($Na_2SO_4$) and concentrating under reduced pressure. The residue is purified on a silica column (eluent: EtOAc/heptane 1/4) in order to produce a white solid.

NMR $^1$H (DMSO d6, 400 MHz, δ): 0.79 (d, 3H); 1.05 (m, 2H); 1.26 (m, 1H); 1.57 (d, 2H); 2.18 (t, 2H); 3.56 (d, 2H); 4.89 (s, 2H); 7.6 (m, 3H); 7.68 (s, 1H); 7.88 (m, 4H).

29.3) 3-(4-methylpiperidinosulphonyl)benzylamine:

Intermediate 29.2 is treated with an excess of hydrazine hydrate in methanol and the resulting mixture is maintained under stirring at ambient temperature overnight, then concentrated under reduced pressure. The residue taken up in dichloromethane is washed with a saturated solution of sodium chloride. After drying and concentrating, a white solid is obtained which is purified on a silica column (eluent: 10% MeOH/DCM) in order to produce a white solid.

NMR $^1$H (DMSO-$d_6$, 400 MHz, δ): 0.84 (d, 3H); 1.13 (m, 2H); 1.26 (m, 1H); 1.63 (d, 2H); 2.17 (t, 2H); 3.58 (d, 2H); 4.22 (d, 2H); 7.6 (m, 3H); 7.70 (s, 1H).

29.4) 3,7-dihydroxy-N-{3-[(4-methyl-1-piperidinyl)sulphonyl]benzyl}-2-naphthamide:

The experimental protocol used is the same as that described for the compound of Example 11, intermediate 29.3 replacing 4-nitrophenethylamine.

NMR $^{13}$C (DMSO-$d_6$, 100 MHz, δ): 21.4; 29.39; 32.90; 42.41; 46.19; 109.22; 111.06; 118.89; 121.59; 126.06; 126.14; 127.47; 127.57; 128.07; 129.58; 130.89; 132.15; 136.01; 140.98; 153.00; 153.67; 168.58.

MH+=455.20; r.t.=9.90 min (elution conditions IV).

Example 30

5-(4-{[(1E)-amino(2-thienyl)methylidene]amino}phenyl)-N-[2-(dimethylamino)phenyl]pentanamide hydrochloride 30.1) N-[2-(dimethylamino)phenyl]-5-(4-nitrophenyl)pentanamide:

The experimental protocol used is the same as that described for intermediate 5.1), N,N-dimethyl-1,2-benzenediamine replacing 4-(N-methylpiperazinyl)aniline and 5-(4-nitropheny)pentanoic acid replacing 4-(4-nitrophenyl)butanoic acid.

30.2) 5-(4-aminophenyl)-N-[2-(dimethylamino)phenyl]pentanamide:

The experimental protocol used is the same as that described for intermediate 5.2, intermediate 30.1 replacing intermediate 5.1.

30.3) 5-(4-{[(1E)-amino(2-thienyl)methylidene]amino}phenyl)-N-[2-(dimethylamino) phenyl]pentanamide hydrochloride:

0.071 g (0.24 mmol) of S-methyl-2-thiophenethiocarboximide hydroiodide (*Ann. Chim.* (1962), 7, 303–337) is added to a solution of 0.07 g (0.22 mmol) of intermediate 30.2 in 2-propanol (5 ml). After heating at 60° C. for 18 hours, the reaction mixture is concentrated to dryness under reduced pressure. The residue is taken up in ethyl acetate and a saturated solution of sodium carbonate. After decanting, the organic phase is washed successively with twice 25 ml of water and twice 25 ml of a saturated solution of sodium chloride. The organic phase is dried over magnesium sulphate followed by filtering and evaporating under reduced pressure. The evaporation residue is purified on a silica column (eluent: ethyl acetate/heptane: 2/1). 0.06 g (yield of 63%) of a free base is obtained. The hydrochloride is prepared by dissolving 0.06 g (0.14 mmol) of the previously obtained base in acetone (10 ml) and by adding 0.43 ml of a molar solution of hydrochloric acid in anhydrous diethyl ether to it. The crystals obtained are filtered and rinsed with diethyl ether in order to produce, after drying, 0.052 g of the desired product (yield of 74%) in the form of a beige solid. Melting point: 145–148° C.

MH+=421.20; r.t.=3.30 min (elution conditions II).

Example 31

3-({4-[(4-methylphenyl)sulphonyl]piperazin-1-yl}carbonyl) naphthalene-2,6-diol 31.1) tert-butyl 4-(3,7-dihydroxy-2-naphthoyl)piperazine-1-carboxylate:

The experimental protocol used is the same as that described for the compound of Example 11, N-tert-butyloxycarbonylpiperazine replacing 4-nitrophenethylamine. A beige solid is obtained.

31.2) 3-(piperazin-1-ylcarbonyl)naphthalene-Z 6-diol:

10 ml of a 4N solution of hydrochloric acid in dioxane is added to a solution of 1.9 g (5 mmol) of intermediate 31.1 in ethanol (20 ml). The solution is stirred for 2 hours at ambient temperature, the solvent is evaporated off and the residue is taken up in dichloromethane. The precipitate is filtered followed by washing with dichloromethane and drying under vacuum. 1.35 g of the expected product is obtained in the form of a white powder.

31.3) 3-({4-[(4-methylphenyl)sulphonyl]piperazin-1-yl}carbonyl) naphthalene-2,6-diol:

The experimental protocol used is the same as that described for the compound of Example 16, intermediate 31.2 replacing the compound of Example 15 and paratoluene sulphonyl chloride replacing methane sulphonyl chloride. A yellow powder is obtained.

Melting point: 135–137° C.

MH+=427.20; r.t.=8.30 min (elution conditions IV).

The Compounds of Examples 32 and 33 are Synthesized According to the Same Strategy as that Used for the Compound of Example 31.

Example 32

3-{[4-(methylsulphonyl)piperazin-1-yl]carbonyl}naphthalene-2,6-diol

Yellow powder. Melting point: 124–126° C.
MH+=351.20; r.t.=6.70 min (elution conditions IV).

Example 33

3-{[4-(butylsulphonyl)piperazin-1-yl]carbonyl}naphthalene-2,6-diol

Yellow powder. Melting point: 105–110° C.
MH+=393.20; r.t.=7.90 min (elution conditions IV).

Pharmacological Study of the Compounds of the Invention

Test Protocols a) Measurement of the Phosphatase Activity of the Purified Cdc25C Recombinant Enzyme The phosphatase activity of the MBP-Cdc25C protein is evaluated by the dephosphorylation of 3-O-methylfluorescein-phosphate (OMFP) to 3-O-methylfluorescein (OMF) with determination of the fluorescence of the reaction product at 475 nm. This test allows identification of the inhibitors of cdc25 recombinant enzyme. The preparation of the fusion protein MBP-cdc25C is described in PCT Patent Application WO 01/44467.

The reaction is carried out in 384-well plate format in a final volume of 50 µl. The MBP-Cdc25C protein (prepared as described above) is stored in the following elution buffer: 20 mM Tris-HCl pH 7.4; 250 mM NaCl; 1 mM EDTA; 1 mM DTT; 10 mM maltose. It is diluted to a concentration of 60 µM in the following reaction buffer: 50 mM Tris-HCl pH 8.2; 50 mM NaCl; 1 mM DTT; 20% glycerol. Measurement of the background noise is carried out with the buffer without addition of the enzyme. The products are tested at decreasing concentrations starting from 80 µM. The reaction is initiated by the addition of an OMFP solution at 500 µM final (prepared beforehand from a 12.5 mM stock solution in 100% DMSO (Sigma #M2629)). After 4 hours at 30° C. in a disposable 384-well plate, the fluorescence measured at OD 475 nm is read using a Victor2 plate reader (EGG-Wallac). Determination of the 50% inhibitory concentration of the enzymatic reaction is calculated from three independent experiments. Only the values included in the linear part of the sigmoid are retained for linear regression analysis.

b) Measurement of the State of cdc2 Phosphorylation:

This relates to showing that the enzymatic activity of cdc25-C phosphatase is inhibited in vivo on the purified enzyme in the presence of selected inhibitors. When cdc25-C is inhibited, the quantity of phosphorylated cdc2 protein (inactive) increases.

The cells of the Mia PaCa2 line are seeded at a rate of 450 000 cells in 10 cm Petri dishes in Dulbecco's modified Eagle medium completed with 10% foetal calf serum. 48 hours later, the cells are treated for 1 hour with the compound to be tested or menadione at 100 µM (reference inhibitor). The medium is renewed after washing with PBS. 24 hours after the cells are scraped and lysed in the lysis buffer (Hepes 50 mM pH 7.5; NaCl 10 mM; Triton X100 1%; glycerol 10%; MgCl$_2$ 5 mM; EDTA 1 mM; sodium orthovanadate 1 mM; protease inhibitor cocktail 1836170 Roche Diagnostics). After centrifugation at 13 000 rpm for 10 minutes at 4° C., the concentration of proteins is determined in the supernatant (Bio-Rad DC Protein assay kit) and adjusted to 10 µg.

The load buffer concentrated 5 times (Tris HCl 125 mM pH 7.4; SDS 10%; glycerol 50%; bromophenol blue 0.025%; β-mercaptoethanol 7%) is added to the samples. The samples are heated for 10 minutes at 100° C. The samples are deposited in a volume of 40 μl on Tris/Glycine 12% gels (BioRad). Migration occurs over 1 hour at 180 V. The proteins are transferred onto a nitrocellulose membrane (Hybond C, Amersham) under semi-dry conditions. The membrane is blocked for 1 hour in milk (BioRad) at 5% with 0.1% Tween 20. Then it is incubated for 6 hours with the primary antibody directed against phosphorylated cdc2 (PhosphoPlus cdc2, 91115 New England BioLabs) diluted to $1/1300^{th}$. After washing in PBS-Tween 20 at 0.1%, the membrane is incubated for 1 hour and 30 minutes with the secondary antibody anti-rabbit Immunoglobulin G (anti-rabbit IgG-HRP, sc2030, Santa Cruz) diluted to $1/40000^{th}$. The proteins are revealed by electrochemical luminescence (western blotting detection system $ECL^+$, Amersham) which is detected using photographic films (BioMax light, Sigma). The images are scanned (BioProfil scanner, Vilbert Lourmat) and processed in Powerpoint®. The result obtained is reproduced in FIG. 1 which represents the comparative effect of menadione and the compound of Example 1 on the phosphorylation of cdc2 in the Mia PaCa-2 line (3 hour treatment with menadione or the compound of Example 1 and sampling 24 hours later).

c) Characterization of the Anti-proliferative Activity:

By way of example, the effect of a treatment on two lines of human Mia-Paca2 and DU145 cells with compounds of Examples 1–5 described previously will be studied. The cell lines DU145 (human prostate cancer cells) and Mia-PaCa2 (human pancreatic cancer cells) were acquired from the American Tissue Culture Collection (Rockville, Md., USA). The cells placed in 80 μL of Dulbecco's modified Eagle medium (Gibco-Brl, Cergy-Pontoise, France) completed with 10% foetal calf serum inactivated by heating (Gibco-Brl, Cergy-Pontoise, France), 50000 units/l of penicillin and 50 mg/l streptomycin (Gibco-Brl, Cergy-Pontoise, France), and 2 mM of glutamine (Gibco-Brl, Cergy-Pontoise, France) were seeded on a 96-well plate on day 0. The cells were treated on day 1 for 96 hours with increasing concentrations of each of the compounds to be tested up to 50 μg/ml. At the end of this period, quantification of cell proliferation is evaluated by a colorimetric test based on the cleavage of the tetrazolium salt WST1 by mitochondrial dehydrogenases in viable cells leading to the formation of formazan (Boehringer Mannheim, Meylan, France). These tests are carried out in duplicate with 8 determinations per concentration tested. For each compound to be tested, the values included in the linear part of the sigmoid were retained for linear regression analysis and used to estimate the inhibitory concentration $IC_{50}$. The products are solubilized in dimethylsulphoxide (DMSO) at $10^{-2}$ M and finally used in culture with 0.5% DMSO.

Results of the Tests a) The compounds of Examples 1 to 11, 13 to 18 and 27 to 33 present an $IC_{50}$ lower than or equal to 100 μM on the phosphatase activity of the purified Cdc25-C recombinant enzyme.

b) The inhibitory activity of the compound of Example 1 on the endogenous cdc25C phosphatase of human cells is shown by the growing increase of the phosphorylated form of cdc2 in the Mia-Paca2 cells treated with increasing concentrations of this compound. This increase is comparable to that induced by menadione (see FIG. 1).

c) The compounds of Examples 1 to 4, 6 to 11, 13, 14, 16 to 18, 22 and 28 to 31 present an $IC_{50}$ lower than or equal to 100 μM on the cell proliferation of Mia-Paca2 lines.

d) The compounds of the examples 1 to 4, 8 to 10, 13, 14, 16 to 18, 22 and 28 to 30 present an $IC_{50}$ lower than or equal to 100 μM on the cell proliferation of DU-145 lines.

What is claimed is:

1. A compound of the formula

(III)

wherein A is

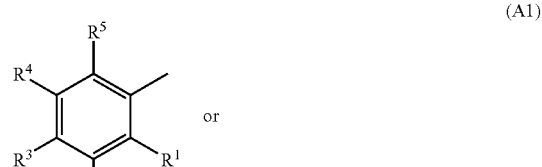

(A1)

or

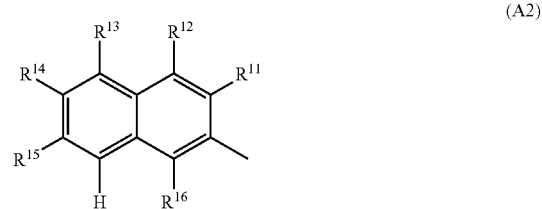

(A2)

two of $R^1$, $R^2$, $R^3$, $R^4$, and $R^5$ are hydrogen the other three are independently selected from the group consisting of hydrogen, halogen, alkyl, hydroxy, alkoxy, alkylcarbonyloxy, alkylthio and $NR^6R^7$, it being understood that:

either $R^1$ and one of $R^2$ and $R^4$ are independently selected from the group consisting of hydroxy, alkylcarbonyloxy and $—NR^6R^7$, or $R^2$ and one of $R^3$ and $R^5$ are independently selected from the group consisting of hydroxy, alkylcarbonyloxy and $—NR^6R^7$, or $R^4$ and one of $R^3$ and $R^5$ are independently selected from the group consisting of hydroxy, alkylcarbonyloxy and $—NR^6R^7$, or one of $R^1$, $R^3$ and $R^5$ is hydroxy, alkylcarbonyloxy, and $—NR^6R^7$, and B—N(W)—X—Y remainder is attached to A by nitrogen, $R^6$ and $R^7$ are independently each time that they occur, hydrogen or alkyl or $R^6$ and $R^7$ together with the nitrogen form a heterocycle with 4 to 7 ring members comprising 1 to 2 heteroatoms, the members necessary to complete the heterocycle being independently selected from the group consisting of $—CR^8R^9—$, $—O—$, $—S—$ and $—NR^{10}—$, $R^8$ and $R^9$ independently are each time that they occur selected from the group consisting of hydrogen, alkyl, alkoxy, benzyloxycarbonylalkylamino and dialkylamino, and $R^{10}$ independently is each time that it occurs hydrogen or alkyl, A is

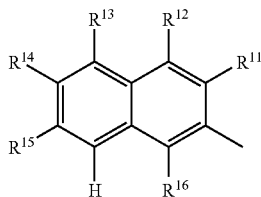
(A2)

$R^{11}$ and one of $R^{13}$, $R^{14}$, and $R^{15}$ are hydroxy while the other $R^{13}$, $R^{14}$ and $R^{15}$ as well as $R^{16}$ are hydrogen;

B is —$(CH_2)_p$— and p is an integer from 0 to 1;

W is selected from the group consisting of hydrogen or alkyl;

X is selected from the group consisting of —$(CH_2)_q$—, —$(CH_2)_q$—NH— and —CO—$(C_2)_r$— [radical], q is an integer from 1 to 6 and r is an integer from 0 to 6;

or B—N(W)—X—Y group is

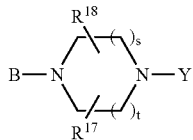

wherein B is as defined above, t is an integer from 0 to 2, s is an integer from 0 to 1 and $R^{17}$ and $R^{18}$ are independently hydrogen or alkyl;

and:

when X is —$(CH_2)_q$— or —CO—$(CH_2)_r$, then Y is

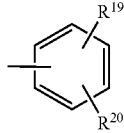

wherein $R^{19}$ is —$SO_2$—,—$NR^{23}R^{24}$, —NH—$SO_2$—$R^{25}R^{24}$ and —O—P(O)($OR^{26}$)$OR^{27}$), $R^{23}$ and $R^{24}$ independently are hydrogen or alkyl, or $R^{23}$ and $R^{24}$ together with the nitrogen which carries them form a heterocycle with 5 to 7 ring members, the additional members of which are independently selected from the group consisting of—$CHR^{28}$—, —$NR^{29}$—, —O— and —S—, $R^{28}$ and $R^{29}$ are independently each time that they occur, hydrogen or alkyl, $R^{25}$ is alkyl, haloalkyl, aryl, heteroaryl, aralkyl and heteroaralkyl, the aryl or heteroaryl nucleus of which is optionally substituted by at least one member independently selected from the group consisting of halogen, alkyl, haloalkyl, hydroxy, alkoxy and nitro, except for the optional nitrogen atoms of the heteroaryl nucleus for which the optional substituents are alkyl, $R^{26}$ and $R^{27}$ are independently alkyl, and $R^{20}$ is hydrogen, halogen, alkyl, alkoxy and alkylthio;

when X is —$(CH_2)$q—NH— or when B—N(W)—X—Y is

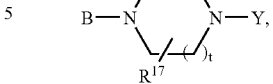

then Y is only —$SO_2$—$R^{30}$, $R^{30}$ is selected from the group consisting of alkyl, haloalkyl, aryl, heteroaryl, aralkyl or heteroaralkyl, the aryl or heteroaryl nucleus of which is optionally substituted by at least one halogen, alkyl, haloalkyl, hydroxy, alkoxy and nitro, except for the optional nitrogen atoms of the heteroaryl nucleus for which the optional substituents are alkyl;

it being understood that when B—N(W)—X—Y is

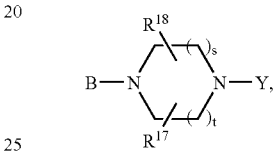

the B is —$(CH_2)$—.

2. A compound of claim 1 selected from the group consisting of:

4-(dimethylamino)-2-({methyl[2-(4-nitrophenyl)ethyl]amino}methyl)phenol;

4-(dimethylamino)-2-methoxy-6-({[2-(4-nitrophenyl)ethyl]amino}methyl)phenol;

4-(dimethylamino)-2-({[2-(4-nitrophenyl)ethyl]amino}methyl)phenol;

2-(dimethylamino)-6-methoxy-4-({methyl[2-(4-nitrophenyl)ethyl]amino}-methyl)phenol;

2-({methyl[2-(4-nitrophenyl)ethyl]amino}methyl)-1,4-benzenediol;

4-(dimethylamino)-2-methoxy-6-({methyl[2-(4-nitrophenyl)ethyl]amino}methyl)phenyl acetate;

and a salt thereof.

3. A pharmeceutical composition comprising a compound according to claim 1 and a pharmaceutically acceptable salt thereof.

4. A composition of claim 1, wherein the compound is selected from the group consisting of:

4-(dimethylamino)-2-methoxy-6-({methyl[2-(4-nitrophenyl)ethyl]amino}-methyl)phenol;

4-(dimethylamino)-2-({methyl[2-(4-nitrophenyl)ethyl]amino}methyl)phenol;

4-(dimethylamino)-2-methoxy-6-({[2-(4-nitrophenyl)ethyl]amino}methyl)phenol;

4-(dimethylamino)-2-({[2-(4-nitrophenyl)ethyl]amino}methyl)phenol;

2-(dimethylamino)-6-methoxy-4-({methyl[2-(4-nitrophenyl)ethyl]amino}-methyl)phenol;

2-({methyl[2-(4-nitrophenyl)ethyl]amino}methyl)-1,4-benzenediol;

4-(dimethylamino)-2-methoxy-6-({methyl[2-(4-nitrophenyl)ethyl]amino}methyl)phenyl acetate;

or of a phannaceutically acceptable salt of one of the latter.

5. A composition of claim 1 wherein the compound is 5-(4-{[1E)-amino(2-thienyl)methylidene]amino}phenyl)-N-[2-(dimethylamino) phenyl]pentanamide or a pharmaceutically acceptable salt thereof.

6. A process for the preparation of a compound of claim 1 of the formula

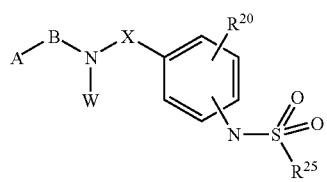
(I).3 wherein A, B, W, X, $R^{20}$ and $R^{25}$ have the definitions of claim 1, comprising reacting a compound of the formula

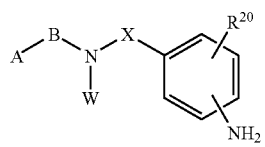
(I).2 with a compound of formula $R^{25}$—$SO_2Cl$ in an aprotic solvent and in the presence of a base.

7. A process for the preparation of a compound of the formula

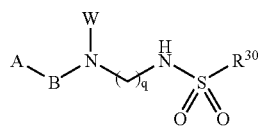
(I).7

A, B, W, q and $R^{30}$ have the definitions of claim 1, comprising reacting a compound of the formula

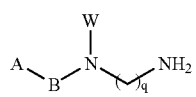
(XXIV)

with a compound of claim 1 of the formula $R^{30}$—$SO_2Cl$ (XXV)

in an aprotic solvent and in the presence of a base.

8. A process for the preparation of a compound of claim 1 of the formula

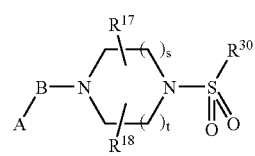
(I).8 wherein A, B, W, q and $R^{30}$ have the definitions of claim 1, comprising reacting a compound of claim 1 having the formula

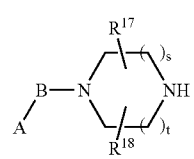
(XXII)a with a compound of the formula $R^{30}$—$SO_2Cl$ (XXV)

in an aprotic solvent and in the presence of a base.

9. A process for the preparation of a compound of claim 1 of the formula

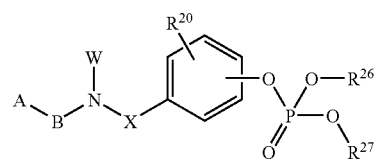
(I).9 wherein A, W, X, $R^{20}$, $R^{26}$, and $R^{27}$ have the definition of claim 1, and B is —CO— or —$CH_2$— comprising reacting an amine of the formula

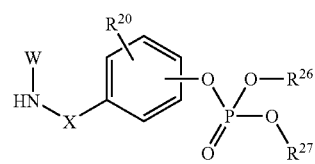
(IV)p and B is —$CH^2$—, with an aldehyde of the formula

A—CHO (VI)

in an alcoholic solvent and in the presence of a reducing agent.

* * * * *